United States Patent
He et al.

(10) Patent No.: US 7,640,061 B2
(45) Date of Patent: Dec. 29, 2009

(54) ELECTRONIC MODULE DESIGN TO MAXIMIZE VOLUME EFFICIENCY

(75) Inventors: Tom X. He, Simi Valley, CA (US); Matthew I. Haller, Valley Village, CA (US); Jordi Parramon, Valencia, CA (US); Goran N. Marnfeldt, Hollviken (SE)

(73) Assignee: Boston Scientific Neuromodulation Corporation, Valencia, CA (US)

(*) Notice: Subject to any disclaimer, the term of this patent is extended or adjusted under 35 U.S.C. 154(b) by 491 days.

(21) Appl. No.: 11/545,334

(22) Filed: Oct. 10, 2006

(65) Prior Publication Data

US 2007/0073360 A1 Mar. 29, 2007

Related U.S. Application Data

(62) Division of application No. 10/609,452, filed on Jun. 27, 2003, now Pat. No. 7,120,992.

(60) Provisional application No. 60/392,475, filed on Jun. 28, 2002.

(51) Int. Cl.
*A61N 1/375* (2006.01)

(52) U.S. Cl. ............... 607/36; 29/846; 361/679.01; 361/735

(58) Field of Classification Search ............ None
See application file for complete search history.

(56) References Cited

U.S. PATENT DOCUMENTS

| | | | | | |
|---|---|---|---|---|---|
| 4,614,194 | A | * | 9/1986 | Jones et al. ............ | 607/2 |
| 4,616,655 | A | * | 10/1986 | Weinberg et al. ........ | 607/2 |
| 5,068,708 | A | * | 11/1991 | Newman ............... | 257/668 |
| 5,256,590 | A | * | 10/1993 | Inoue .................. | 438/454 |
| 5,990,545 | A | * | 11/1999 | Schueller et al. ........ | 257/697 |
| 6,768,190 | B2 | * | 7/2004 | Yang et al. ............. | 257/686 |
| 2003/0141582 | A1 | * | 7/2003 | Yang et al. ............. | 257/686 |
| 2004/0033673 | A1 | * | 2/2004 | Cobbley et al. ......... | 438/455 |
| 2005/0194674 | A1 | * | 9/2005 | Thomas et al. ......... | 257/690 |
| 2006/0267173 | A1 | * | 11/2006 | Takiar et al. .......... | 257/686 |

* cited by examiner

*Primary Examiner*—Kennedy J Schaetzle
(74) *Attorney, Agent, or Firm*—Wong, Cabello, Lutsch, Rutherford & Brucculeri, LLP

(57) ABSTRACT

Compact electronic modules, which may be used with implantable microstimulators and other medical and non-medical devices, and manufacture/assembly of such modules are described. Component and circuitry designs utilize unique redistribution techniques and attachment methods. A number of component designs and packaging configurations maximize the volume efficiency of electronic modules. Also included are improved processes and systems enabling the manufacture and assembly of such compact packages.

22 Claims, 26 Drawing Sheets

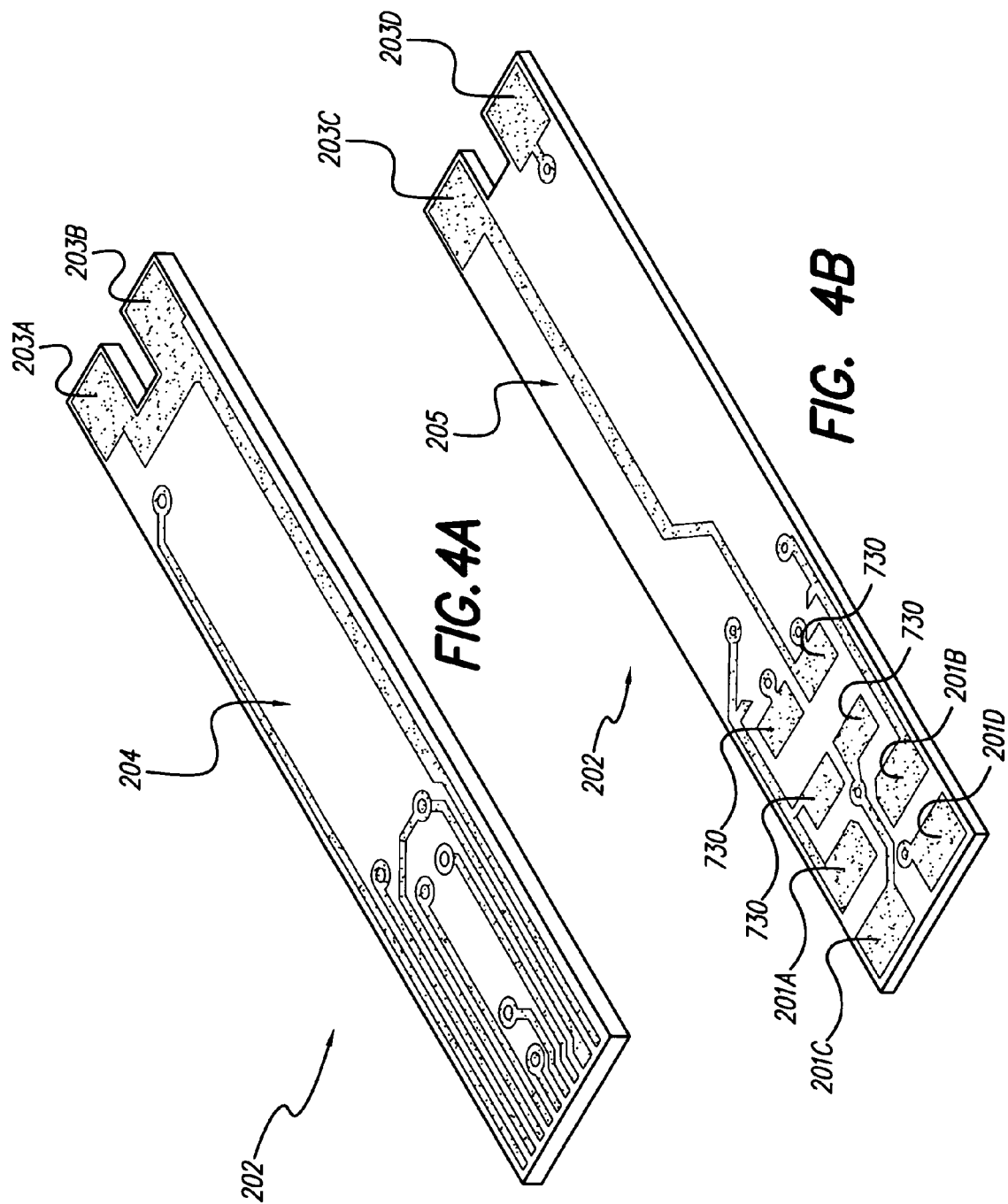

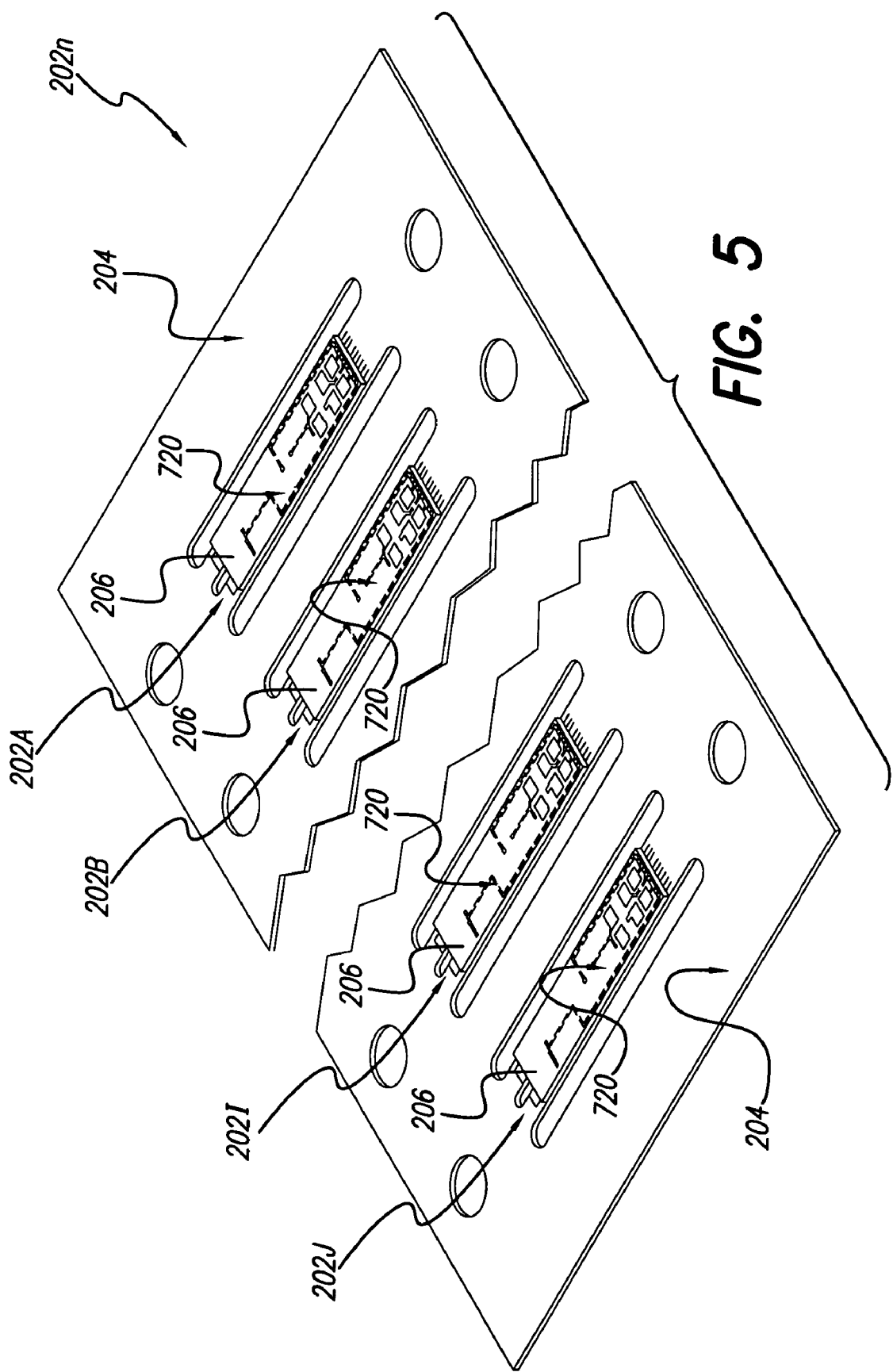

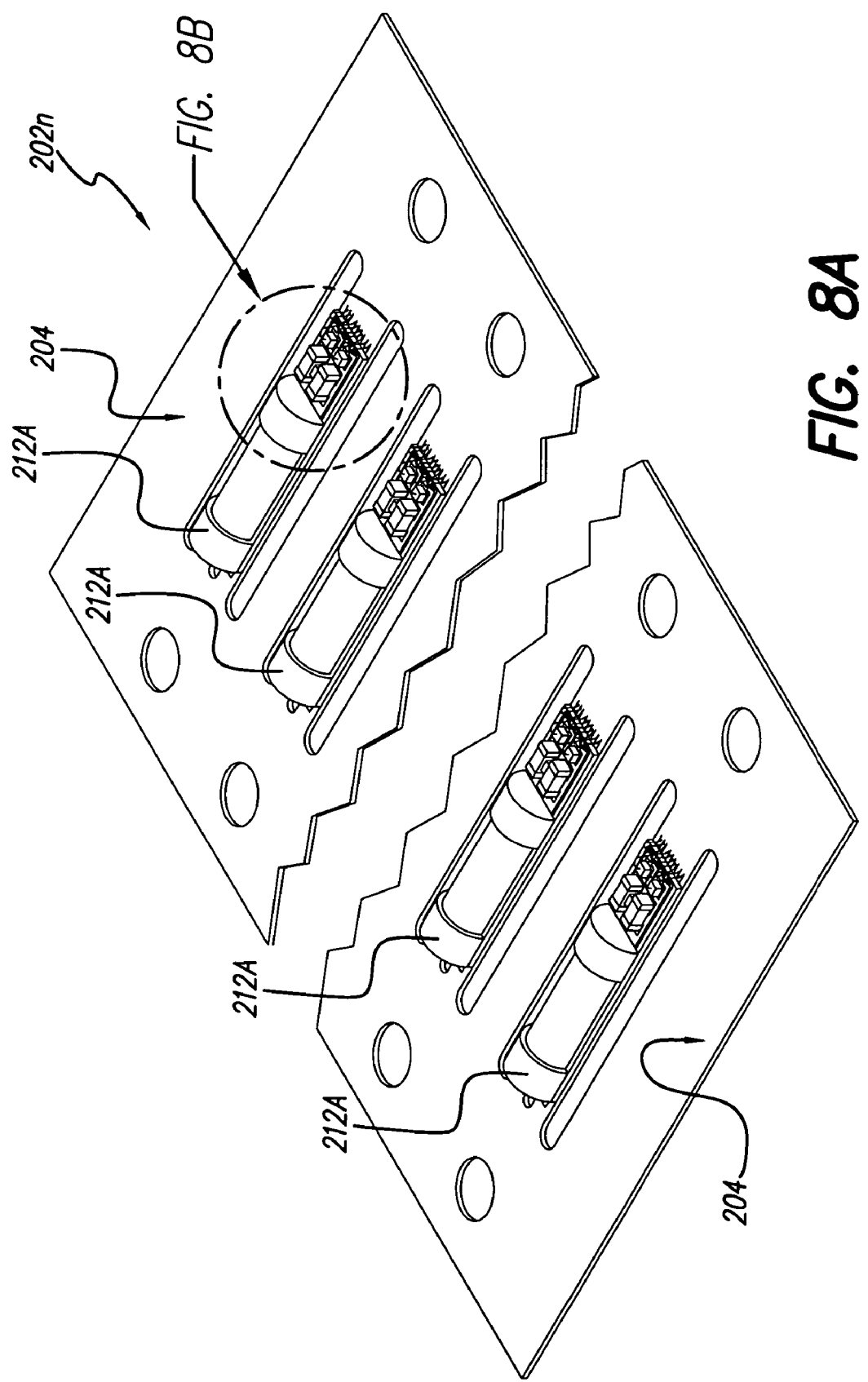

ELECTRONIC MODULE DESIGN TO MAXIMIZE VOLUME EFFICIENCY

The present application is a divisional of U.S. patent application Ser. No. 10/609,452, filed Jun. 27, 2003 (now U.S. Pat. No. 7,120,992), which claims the benefit of U.S. Provisional Patent Application Ser. No. 60/392,475, filed Jun. 28, 2002. These applications are incorporated herein by reference in their entireties.

FIELD OF THE INVENTION

The present invention generally relates to compact electronic modules and more particularly to component and circuitry designs utilizing redistribution techniques; attachment methods, and other packaging that maximizes the volume efficiency of electronic modules, and further relates to improved processes and systems enabling the manufacture and assembly of such compact packages.

BACKGROUND OF THE INVENTION

Many devices can benefit from optimization of space required for electronic modules, which may allow miniaturization of the device itself and/or introduction or enlargement of other device components. Compact electronic modules are particularly useful for devices requiring volume efficiency, including medical devices and consumer electronics devices. For instance, optimization of the packaging of an electronic module in a transistor radio would allow the entire radio to be more compact. Alternatively or additionally, the freed-up space could be used by other components, such as a larger battery. As another example, the size of implantable medical devices is preferably minimized to reduce trauma, cosmetic, and other effects of a device located in the body. Optimization of the packaging of an electronic module in an implantable medical device would allow the device to be smaller and/or allow the device to accommodate additional and/or larger components.

For example, implantable microstimulators known as Bion® devices are characterized by a small, cylindrical housing which contains electronic circuitry that produces electric currents between spaced electrodes. These microstimulators are implanted proximate to target tissue, and the currents produced by the electrodes stimulate the tissue to reduce symptoms or otherwise provide therapy for various disorders. A compact electronic module would allow a Bion device to be smaller and thus easier to implant and less noticeable and/or allow the device to accommodate additional and/or larger components, such as a larger rechargeable battery that would lengthen time between recharges.

Radio-frequency powered and battery powered microstimulators are described in the art. See, for instance, U.S. Pat. Nos. 5,193,539 ("Implantable Microstimulator); 5,193,540 ("Structure and Method of Manufacture of an Implantable Microstimulator"); 5,312,439 ("Implantable Device Having an Electrolytic Storage Electrode"); 6,185,452 ("Battery-Powered Patient Implantable Device"); 6,164,284 and 6,208,894 (both titled "System of Implantable Device for Monitoring and/or Affecting Body Parameters"). The '539, '540, '439, '452, '284, and '894 patents are incorporated herein by reference in their entirety.

Microstimulators to prevent and/or treat various disorders are taught, e.g., in U.S. Pat. Nos. 6,061,596 ("Method for Conditioning Pelvis Musculature Using an Implanted Microstimulator"); 6,051,017 ("Implantable Microstimulator and Systems Employing the Same"); 6,175,764 ("Implantable Microstimulator System for Producing Repeatable Patterns of Electrical Stimulation"); 6,181,965 ("Implantable Microstimulator System for Prevention of Disorders"); 6,185,455 ("Methods of Reducing the Incidence of Medical Complications Using Implantable Microstimulators"); and 6,214,032 ("System for Implanting a Microstimulator"). The techniques described in these additional patents, including power charging techniques, may also be used with the present inventions. The '596, '017, '764, '965, '455, and '032 patents are incorporated herein by reference in their entirety.

A number of the above cited patents describe microstimulator designs and methods for manufacturing a microstimulator or portions of a microstimulator. Disclosed herein are improved designs and techniques for producing compact electronic modules for a microstimulator or other medical or non-medical device. In addition, the designs and methods disclosed allow such devices, to be manufactured more efficiently, more reliably, and/or more cost effectively.

BRIEF SUMMARY OF THE INVENTION

The present inventions address the above and other needs by providing, inter alia, improved methods for creating compact electronic modules. For instance, a present invention provides component and circuitry designs utilizing a redistribution technique that differ from standard redistribution processes, results, and uses. The technique creates a redistribution surface on the bare integrated circuit (IC) that allows secondary components to be mounted above the IC and connected electrically to the IC through the redistribution surface. The redistribution surface includes mounting pads and other interconnection pads, some along the edge of the redistribution surface to allow simplified connection to a substrate. A further improvement provides electronic shielding within the redistribution surface.

The mounting pads may be positioned via the redistribution surface to one side of the IC, while a portion of the IC and the substrate on which it is mounted are positioned between two halves of a ferrite core. The length and diameter of the ferrite core are thus maximized, while providing the IC and substrate space between the ferrite halves, as well as beyond the ferrite core.

The halves of the ferrite core may further create a dumbbell shape, allowing the wire of the coil to be wound on the center, smaller-diameter portion of the core. The core shape facilitates winding, centering, and protecting the coil, while maximizing the volume of core material and diameter at the ends of the ferrite core. The dumbbell shape further facilitates the creation of a cylindrical device, which is uniquely suited to some uses, such as implantation into a body through a cannula, while also providing the above-stated results.

Methods and means for manufacturing/assembling components into compact electronic modules is described herein. A carrier facilitates manufacturing, assembly, and testing of a small electronic device, and in particular, a small cylindrical device, which includes the compact electronic modules of the invention. For instance, the carrier ensures the coaxial assembly of various components of a cylindrical package. In addition, the carrier protects and eases handling of the device.

Embodiments of the various inventions described herein may include some or all of the items mentioned above. Additional embodiments will be evident upon further review of the present disclosure.

BRIEF DESCRIPTION OF THE DRAWINGS

The above and other aspects of the present inventions will be more apparent from the following more particular description thereof, presented in conjunction with the following drawings wherein:

FIG. 4A is a perspective top view of a substrate panel;

FIG. 4B is a perspective bottom view of the substrate panel of FIG. 4A;

FIG. 5 is a perspective top view of portions of the panel shown in FIG. 3 with an integrated circuit chip attached;

FIG. 8A is a perspective top view of the panel assembly shown in FIG. 7A with the top ferrite half attached;

Corresponding reference characters indicate corresponding components throughout the several views of the drawings.

DETAILED DESCRIPTION OF THE INVENTION

The following description is of the best mode presently contemplated for carrying out the inventions. This description is not to be taken in a limiting sense, but is merely for the purpose of describing the general principles of the inventions. The scope of the presently claimed invention should be determined with reference to the claims.

As described above, the compact electronic modules and methods of manufacture as described and claimed may be used with numerous devices. Such modules and techniques are particularly useful in implantable medical devices, as an example, and as such will be described in conjunction with such an implantable medical device. However, as will be understood by those of skill in the art of electronic devices, such modules and methods may be used with other types of devices.

The exemplary medical device that will be used herein to describe the systems and methods of the inventions is a small, implantable stimulator, and more particularly a battery-powered microstimulator known as a Bion® microstimulator. For purposes of the present disclosure, the battery-powered Bion microstimulator will be referred to as device 10 or microstimulator 10.

The exemplary device 10 has a substantially cylindrical shape (while other shapes are possible) and at least portions of it are hermetically sealed. It includes a processor and other electronic circuitry that allow it to generate stimulus pulses that are applied to a patient through electrodes in accordance with a program that may be stored, if necessary or desired, in programmable memory. The exemplary device 10 also includes a rechargeable battery. The battery is recharged, as required, from an external battery charging system.

Figure 1A:
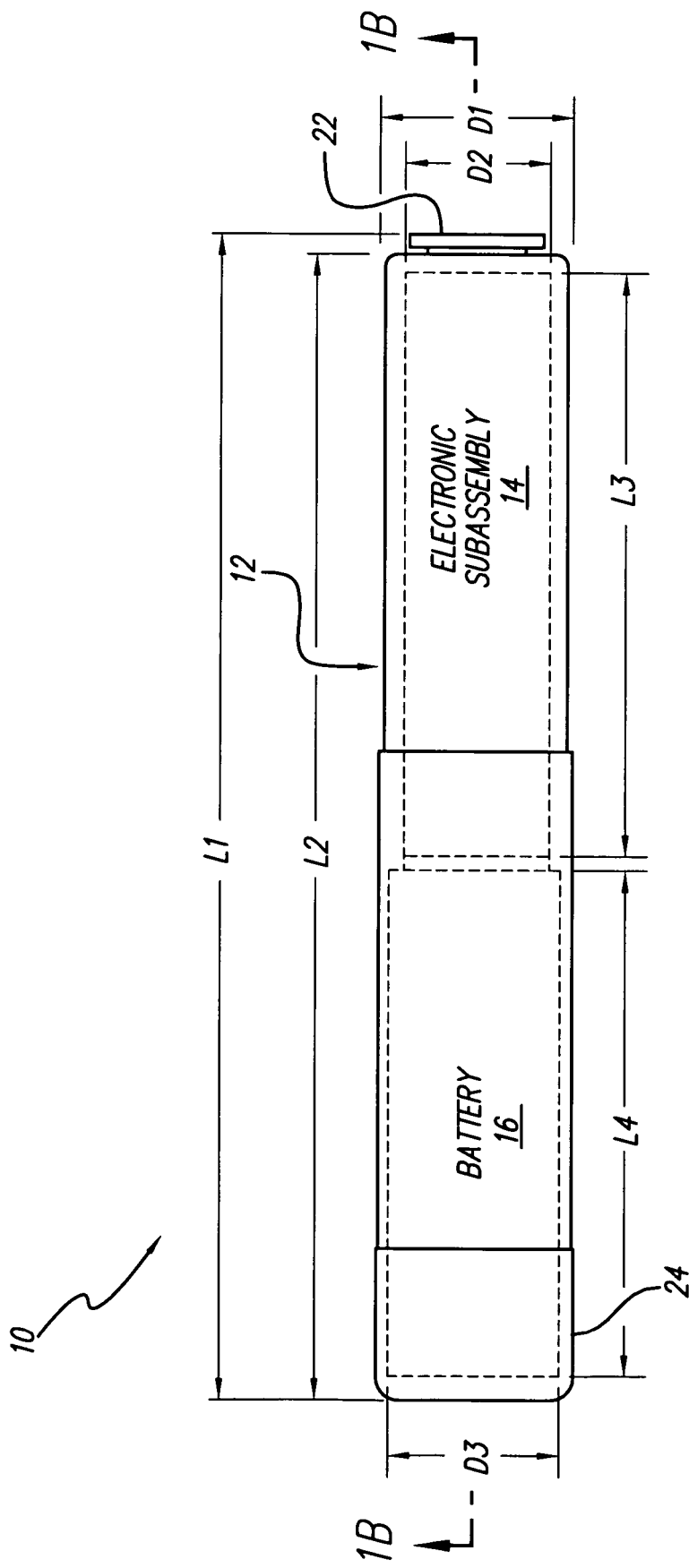
FIG. 1A is a top view of a battery-powered Bion® device used to describe the inventions, showing exemplary dimensions for some components of the device.
Figure 1B:
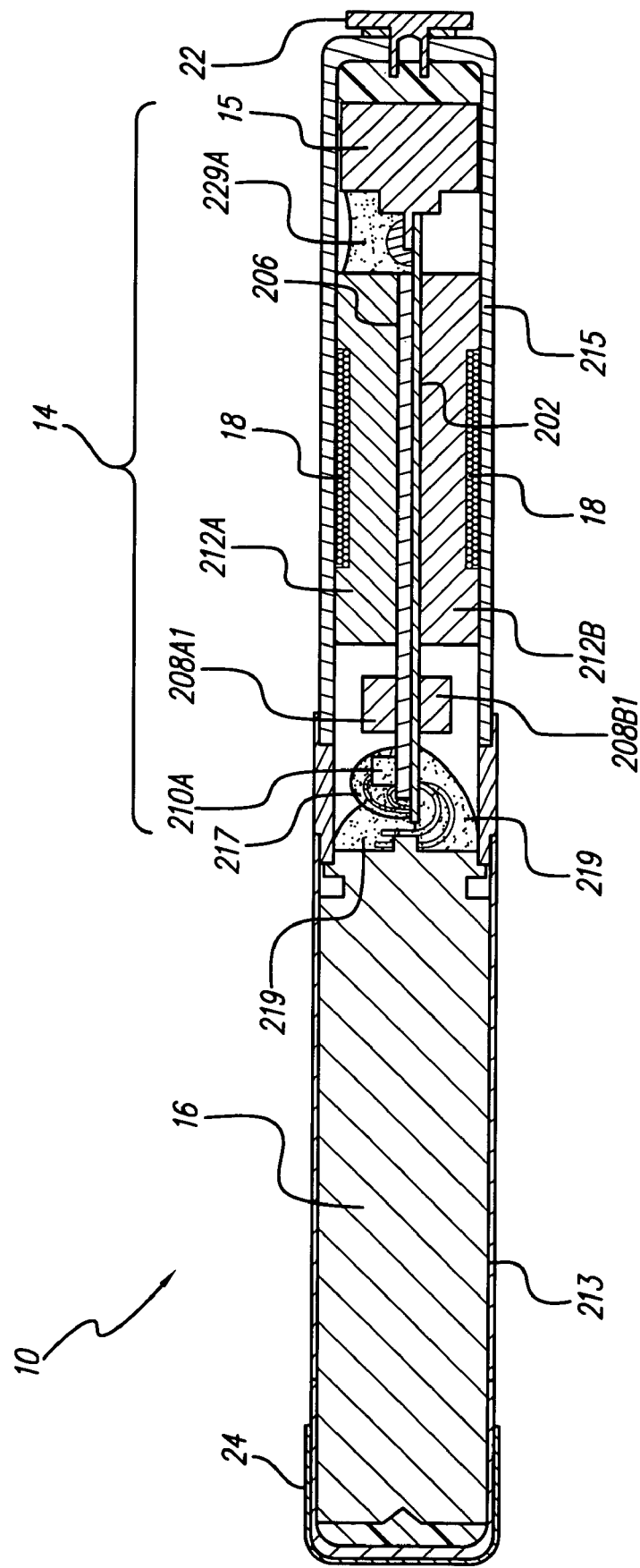
FIG. 1B is a cross-sectional view taken along line 1B-1B of FIG. 1A.

FIG. 1A is a top view of device 10 depicting exemplary overall dimensions for a case 12 and some internal components. As seen in FIG. 1A, the device 10 includes case 12, electronic subassembly 14, power source 16, active/stimulating electrode 22, and indifferent/reference electrode 24. The diagram of FIG. 1A is useful as a simplified representation of the example device 10, depicting just a few of the device components. A cross-section of the assembled device 10 is shown in FIG. 1B. A better understanding of the designs, functions, interactions, and methods of manufacture of various components is provided in the details that follow.

As mentioned above, the exemplary device used herein to describe the inventions is a substantially cylindrical medical device, microstimulator 10. In this exemplary configuration, case 12 has an outer diameter D1 of about 3.20 mm to about 3.30 mm. The inner diameter of the portion of case 12 enclosing electronic subassembly 14 is shown in FIG. 1A as D2. The inner diameter of the portion of case 12 enclosing battery 16 is shown as D3. Inner diameter D2 is about 2.40 mm to about 2.54 mm, and inner diameter D3 is about 2.92 mm to about 3.05 mm.

The length of case 12 plus stimulating electrode 22 is shown in FIG. 1A as L1, and is about 27 mm. Length L2 of case 12 without electrode 22 is about 24.5 mm. The portion of case 12 enclosing electronic subassembly 14 is shown in FIG. 1A as length L3, and has a value of about 13.00 mm. The portion of case 12 enclosing battery 16 is shown in FIG. 1A as length L4, which has a value of about 11.84 mm. Of course, these values can vary. For instance, L1 will change as the type of stimulating electrode 22 changes. As mentioned earlier, the fact that the assemblies and methods described and claimed herein may be used with small devices is one of the advantages of the inventions, but it is in no way limiting. The methods and systems described and claimed may be used with a multitude of devices of varying size and shape. To facilitate understanding of these methods and systems, some components of device 10 and their manufacture/assembly are discussed in detail below.

As shown in FIG. 1A, device 10 includes a power source (e.g., a rechargeable battery 16) and an electronic subassembly 14. Electronic subassembly 14 contains circuitry and other components for, e.g., stimulation, battery charging, telemetry, and production testing. Rechargeable battery 16 is a self-contained rechargeable battery, e.g., a lithium-ion battery, which powers device 10. Battery 16 is recharged, as required, from an external battery charging system (not shown).

Device 10 contains an inductive coil 18 (shown in FIG. 1B) for receiving power for battery charging and for telemetry. Coil 18 may also be utilized to implement additional functions, including voltage conversion/high voltage generation. In the present exemplary configuration, coil 18 has an exemplary cylindrical shape and is constructed from multiple turns of conductive wire wound around a two-piece, dumbbell-shaped ferrite core. Assembly of coil 18 and the two-piece ferrite core, and other electronic components, will be discussed in more detail presently.

Figure 2A:
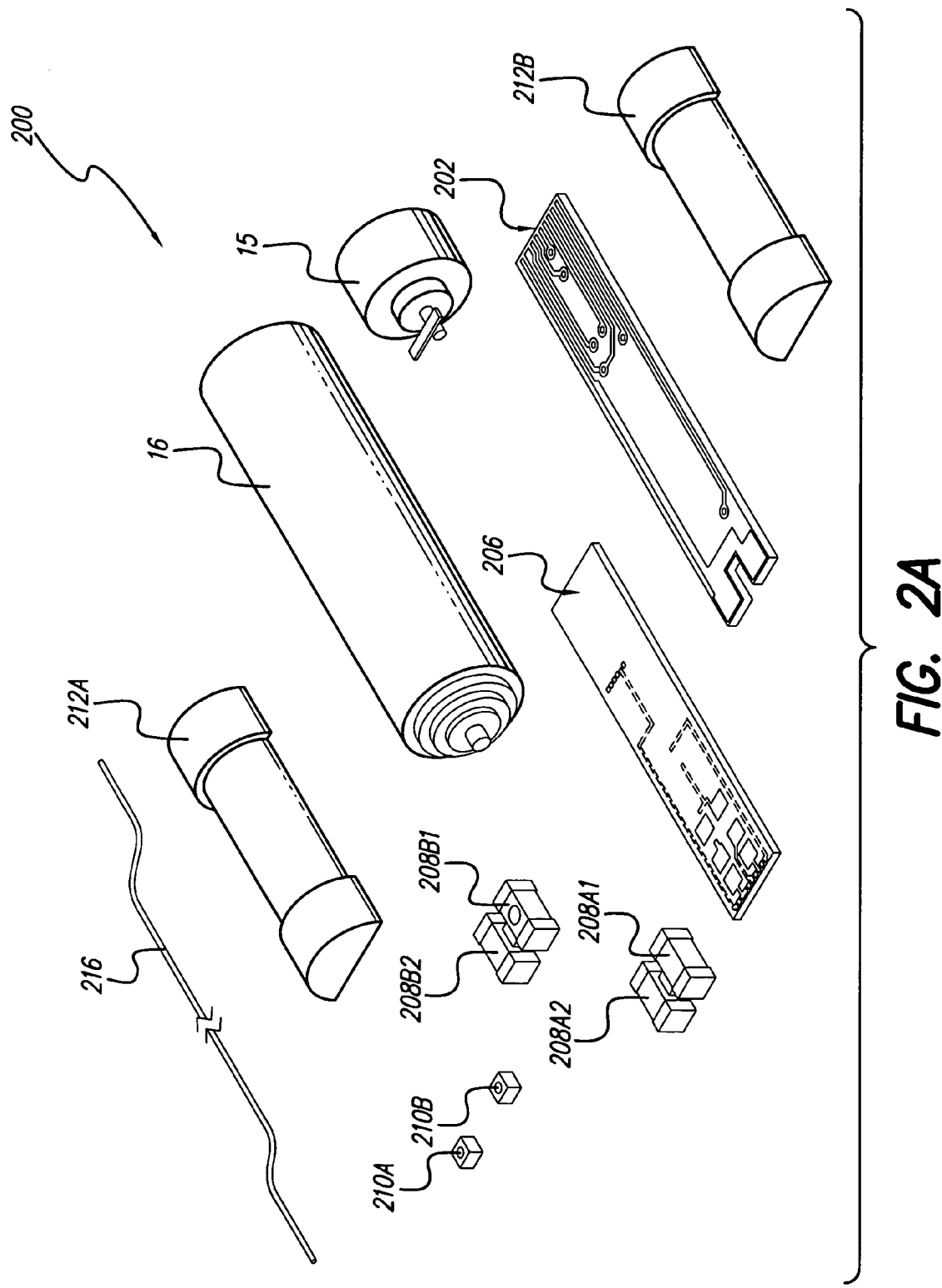
FIG. 2A is an exploded view of the main internal components of the device.
Figure 2B:
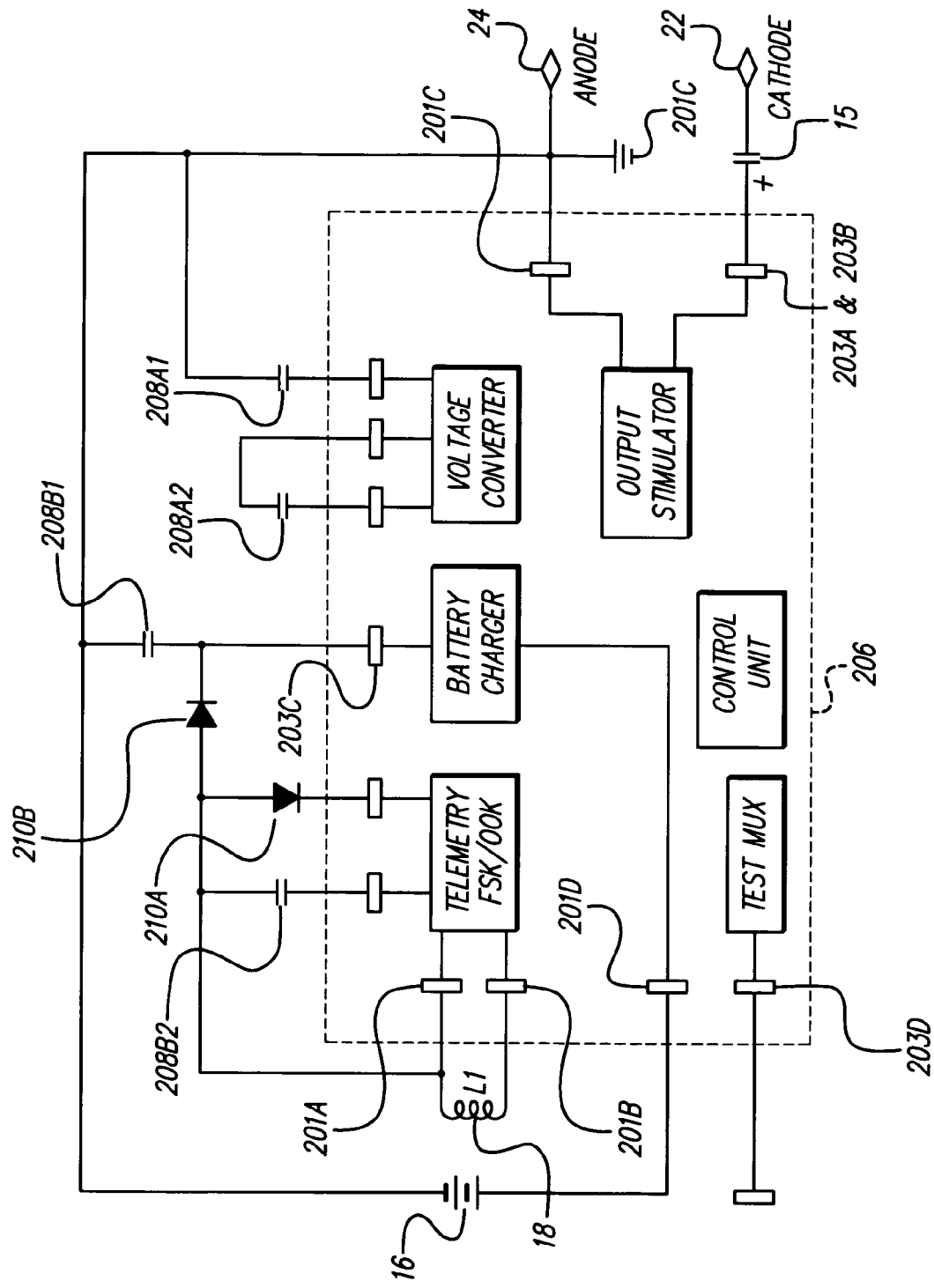
FIG. 2B is a circuit diagram of the interactions of the main components of FIG. 2A.

Some internal components 200 of device 10 are shown unassembled in FIG. 2A, and their interactions once assembled are depicted in the circuit diagram of FIG. 2B. These components 200 include stimulating capacitor 15; battery 16; substrate panel 202; integrated circuit (IC) 206; capacitors 208A1, 208A2, 208B1, and 208B2; diodes 210A and 210B; ferrite halves 212A and 212B; and unwound conductive coil wire 216. Assembly of these components is described below. Portions of the device and its manufacture/assembly are not detailed herein as they are not necessary for describing the inventions. Materials mentioned in the description of the manufacturing/assembly process are exemplary; other suitable materials may be used.

Figure 3:
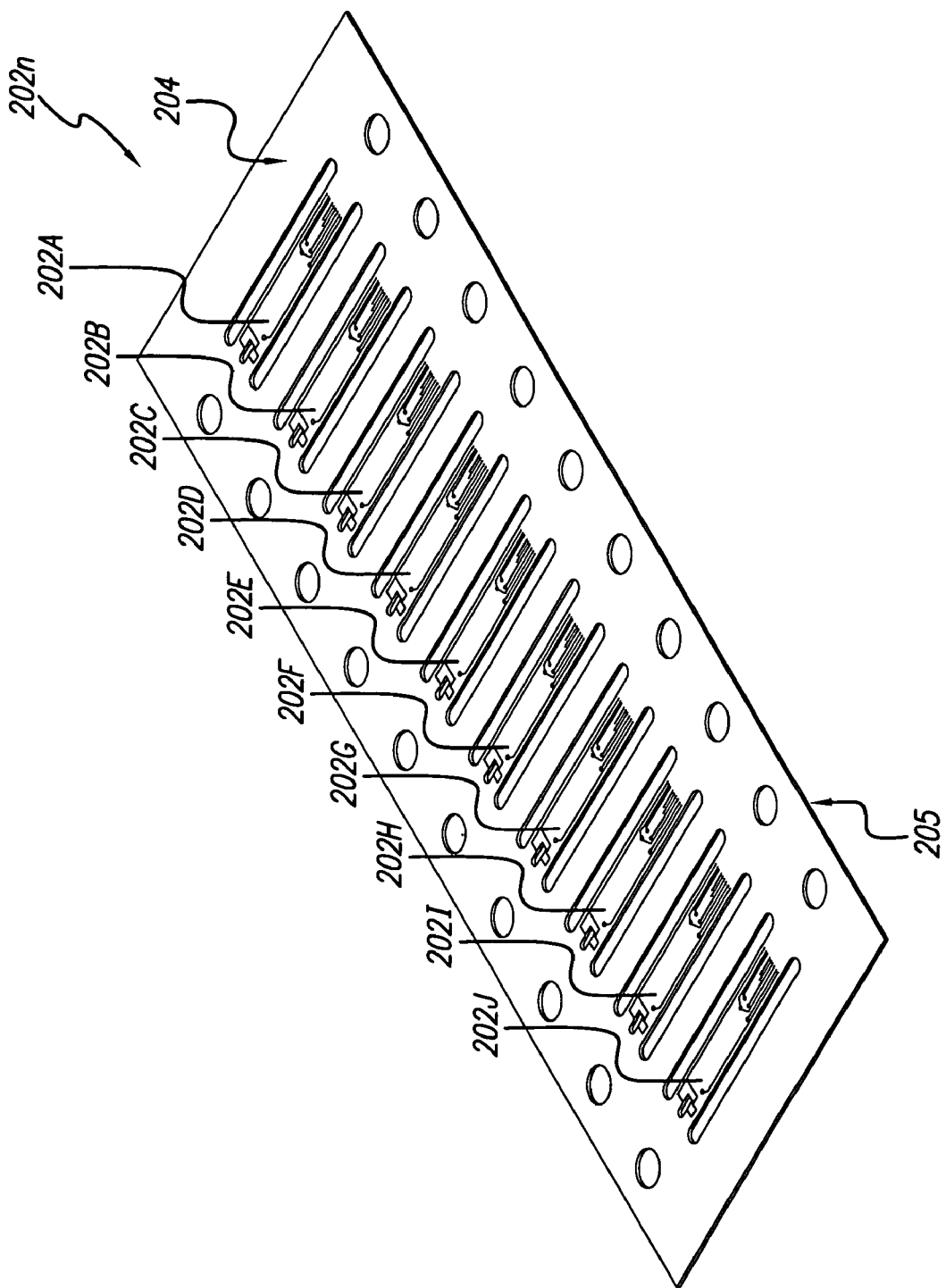
FIG. 3 is a perspective top view of a substrate panel assembly.

As illustrated in FIG. 3, up to ten or more devices may be (but are not necessarily) batch processed for at least a portion of the manufacture/assembly process. Batch processing allows the assembly procedures and testing to be more efficient than assembling each unit individually. FIG. 3 shows substrate panel assembly 202n, which includes substrate panels 202A, 202B, 202C, . . . through 202J, which individual panels are sometimes referred to herein as panel 202 or substrate 202. The contour of each panel 202 of substrate panel assembly 202n may be precut, with only small portions of the edges left attached to substrate panel assembly 202n. The small portions that are left intact aid the alignment of other components and make future singularization of each panel 202 easier, even when other components have been assembled to panel assembly 202n.

Substrate panel assembly 202n is a single layer, double-sided, polyimide-copper circuit board, or other suitable flexible substrate design/material(s). As is common in the art, mounting pads and traces on the top and bottom of the panels (see FIGS. 4A and 4B, respectively) are gold-plated copper or the like and are electrically connected by vias through the panel material. The pads and traces on the top of substrate panels 202 are solderable and wire bondable. The pads on the bottom of panels 202 are solderable.

Substrate panel assembly 202n may be identified by a serial number printed on a portion of the assembly during manufacturing of the panel assembly 202n, while each panel 202 of substrate panel assembly 202n may be uniquely serialized, e.g., using a laser beam. For instance, metal pads 203C and 203D (shown in FIGS. 10B, and 11C), which are used for test probing during several steps of the assembly process, may carry each unique panel serial number.

Figure 10A:
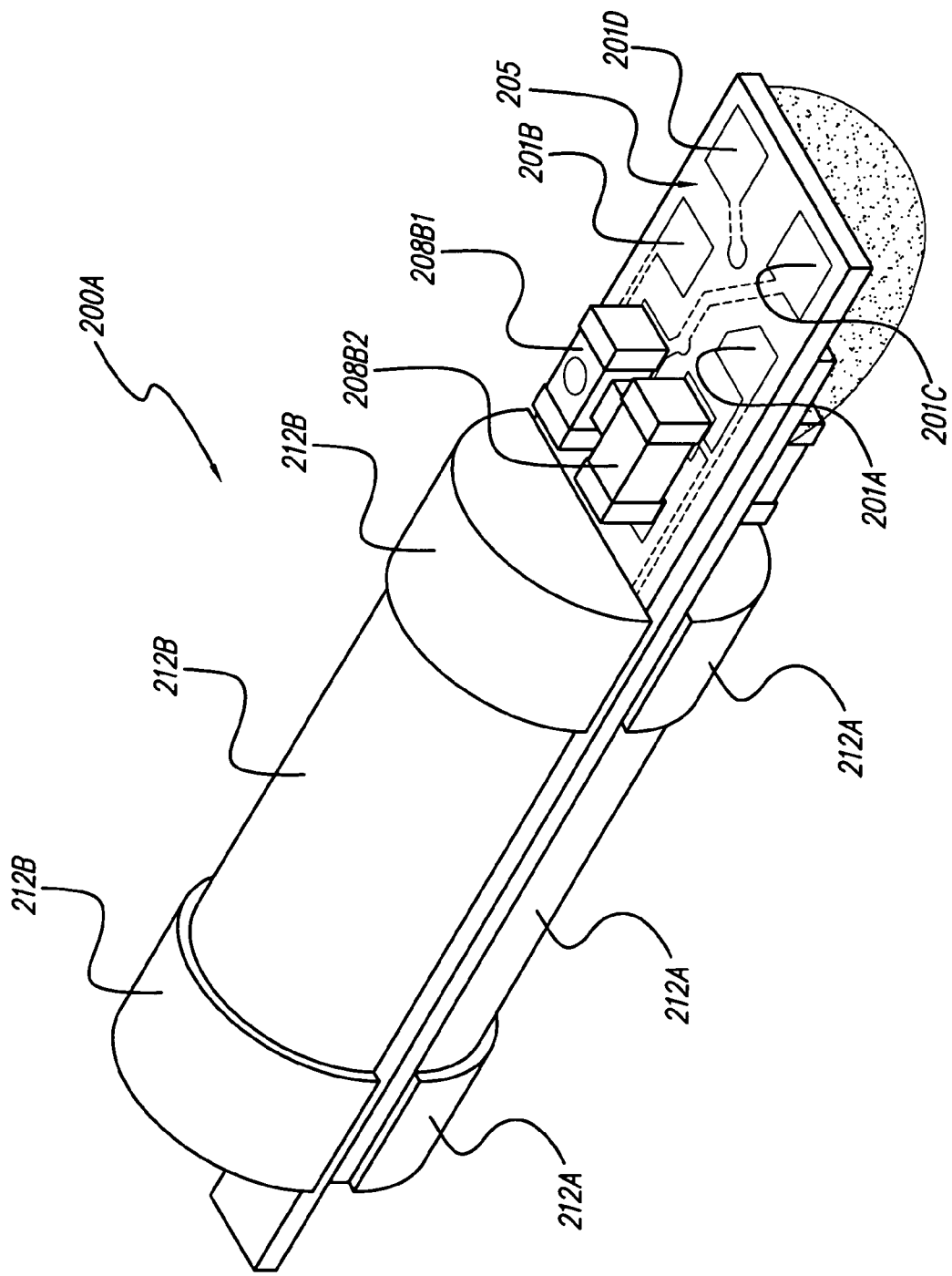
FIG. 10A is a isometric bottom view of the subassembly shown in FIG. 9A.

As seen, e.g., in FIGS. 1B, 5 and 10A, the top and bottom of substrate panel assembly 202n are used to mount other components. As examples, an integrated circuit 206 is mounted to the top 204 of each substrate panel 202 and capacitor 208B1, 208B2 are mounted to the bottom 205 of each substrate panel. All the off-chip, or secondary, components are electrically connected to IC 206 through substrate 202 or through redistributed surface 720, as described below.

Figure 6A:
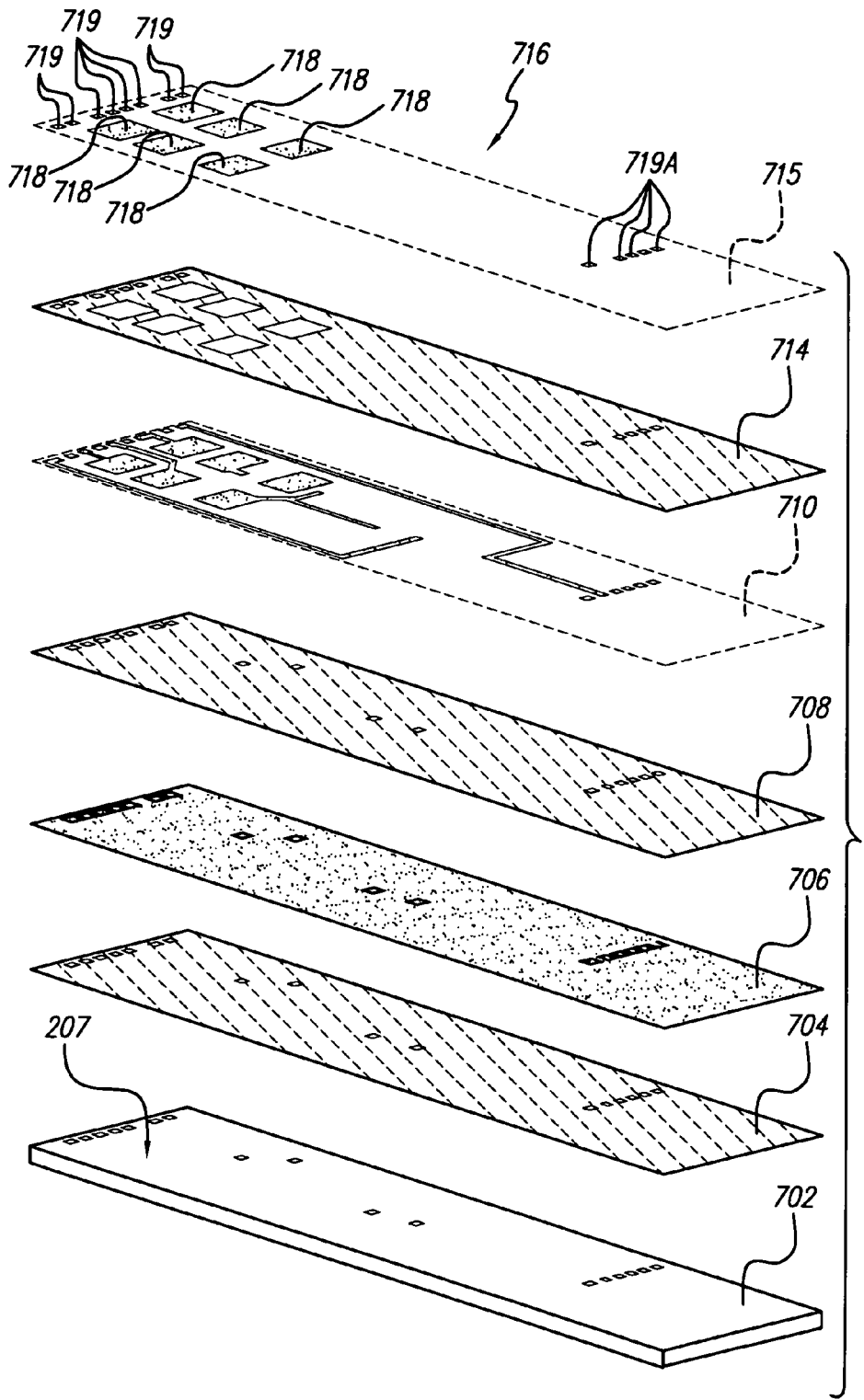
FIG. 6A is an exploded view of one embodiment of layers formed while making a unique redistributed surface on an integrated circuit.
Figure 6B:
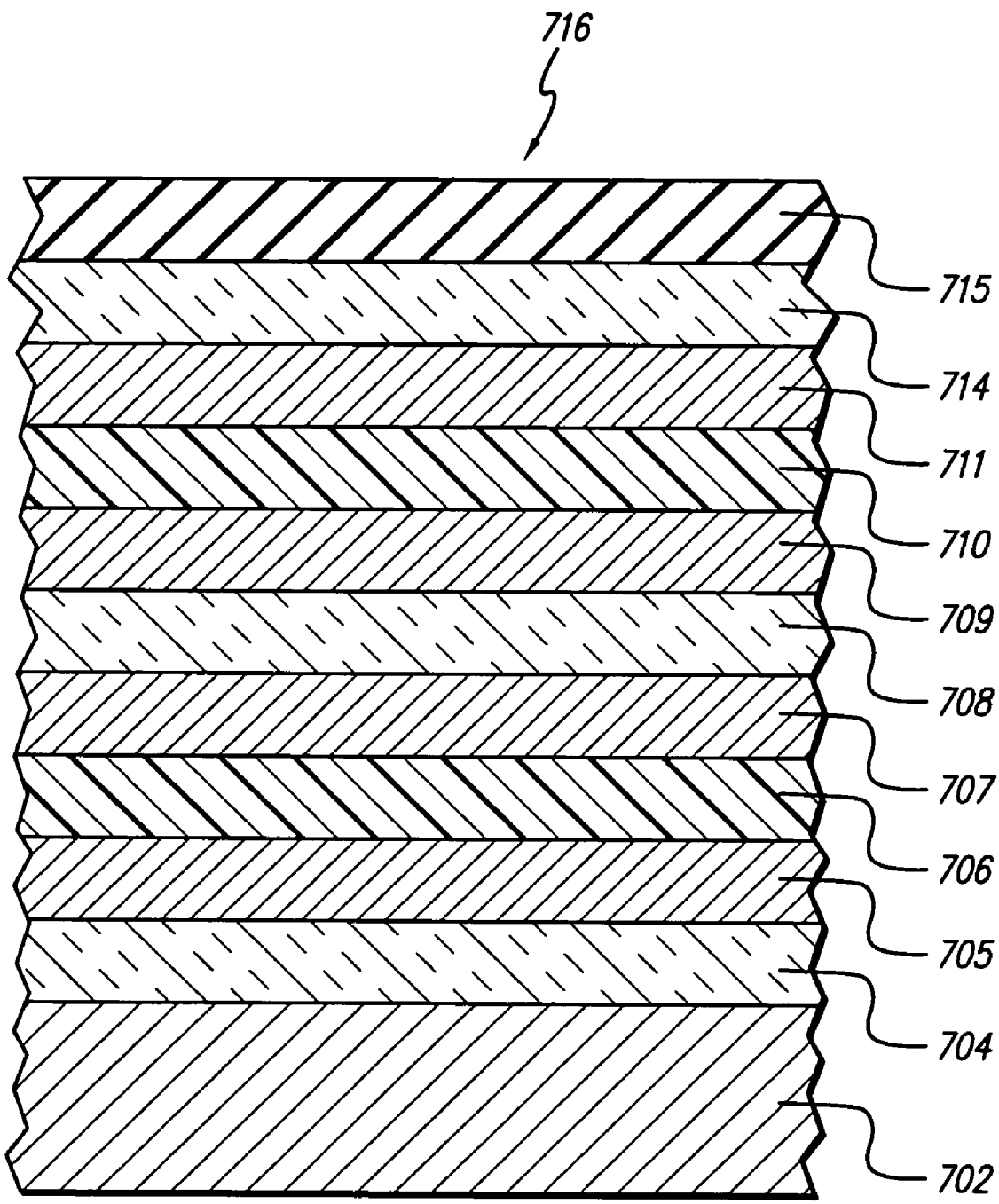
FIG. 6B is a side view of an embodiment of a redistributed surface on an integrated circuit.

Integrated circuit (IC) 206 is a custom designed IC chip (ASIC). The IC wafer includes a multitude of these custom ICs 206. The bare ICs 702 are made using standard IC manufacturing processes. Wafer-level processing reduces production costs by allowing manufacturing and testing of large numbers of ICs at one time. The IC wafer is then taken through a post-process called redistribution, which creates a redistributed surface 720, an example of which is shown in FIGS. 6A and 6B, and as described below:

a) Polyimide (or other suitable insulation) is deposited on the top face 207 of the bare IC 702, if insulation is needed or desired.

b) Photosensitive material such as photoresist is deposited on top of the insulation.

c) The photosensitive material is exposed, e.g., through a mask, in only selected areas (i.e., where the insulation is to remain or is to be removed, depending on whether a "positive" or "negative" process is used), as in photochemical etching processes known in the art.

d) All of the photosensitive material and the portions of the insulation that are not needed are removed, e.g., with a chemical stripping solution. This leaves a first insulation layer 704 where needed, but allows the interconnect pads (aluminum or the like) on the top face 207 of the bare IC to remain exposed.

e) Optionally, a layer of conductive material (e.g., copper) is deposited as a grounding plane 706. When used, grounding plane 706 is ideally positioned between two layers of bond material 705 and 707, such as titanium tungsten. Photosensitive etching or the like is used to remove these materials from around each interconnect pad, leaving all but a ground pad isolated.

f) When grounding plane 706 is used, optional insulation layer 708, of polyimide or the like, is applied (via photochemical etching or the like) to select areas, leaving exposed the interconnect pads.

g) A bond layer 709 of titanium tungsten or the like is deposited to aid the bonding of metal (e.g., copper) redistribution layer 710, if needed or desired. Photosensitive etching or the like may be used at this point, or later, as described below.

h) A layer of copper or other conductive material is deposited. This conductive material (aided by the surrounding layers) creates the traces and mounting/interconnect/test pads, e.g., mounting pads 718 and interconnect pads 719/719A, of the "redistribution" of redistribution layer 710 and redistribution surface 720 that allow, e.g., secondary components such as capacitors 208A1/208A2 and diodes 210A/210B to be assembled above IC 206. This redistribution also simplifies interconnections between IC 206 and substrate 202, as shown in FIG. 12B. Photosensitive etching or the like may be used at this point, or later, as described below.

i) Titanium tungsten or other suitable bonding material is applied to redistribution layer 710 to create bond layer 711, if needed or desired. Photosensitive etching or the like may be used at each layer 709, 710, and 711 individually, or may be used for two or all three of these layers at a time. As such, the material of bond layers 709 and 711 may have the same pattern as redistribution layer 710, or may cover more or less than the redistribution layer material (such as only where two metals overlap).

j) Insulation layer 714 of polyimide or the like is applied (via photochemical etching or the like) to select areas, leaving some conductive areas exposed, e.g., for mounting pads 718 on which secondary components such as capacitors 208A1/208A2 and diodes 210A/210B will be placed.

k) A conductive layer 715 of gold or other conductive material is applied (again, via photochemical etching or the like), if needed or desired, to conductive areas, e.g., mounting pads 718 on which secondary components such as capacitors 208A1/208A2 and diodes 210A/210B will be placed, so may thus be part of a surface layer 716. Conductive layer 715 is preferably (but not necessarily) about 8-10 microns thick when complete, while the other layers of redistributed surface 720 are preferably about 4-5 microns when complete. Depending on the above described options that are used, various "layers", e.g., parts of redistribution layer 710, insulation layer 714, parts of conductive layer 715, may form surface layer 716.

This redistribution process, the resulting redistributed surface 720, and use thereof differ from standard redistribution processes, results, and uses. In standard use, redistribution is used to route connections from peripheral pads into a ball grid array or other area array pattern of "under bump metallurgy" balls that allows the chip to be, for instance, "flipped" onto a printed wire board or other substrate having matching interconnects. The unique redistribution process of the present invention forms a custom-designed layout resulting in a number of mounting pads 718 on which off-chip secondary components are directly mounted, as well as a number of test and interconnect pads 719/719A, some of which are routed to the periphery of the IC.

The resulting configuration of IC 206 (i.e., with redistributed surface 720), substrate 202, and secondary, off-chip components has a number of advantages. Bare IC 702 includes all circuitry that would ordinarily be included or desired in the IC, with no added requirements or detrimental effect to the IC. For instance, bare IC 702 is not constrained by requiring mounting pads in particular positions on the bare IC top face 207 (and/or the packaging is not constrained by having surface mounted components positioned where most convenient for the IC design). The redistributed surface 720 on bare IC 702 contains substrate-like mounting pads 718 above the top face 207 of bare IC 702, which accommodate secondary components that typically require large mounting pads for attachment. This redistributed surface 720 contains larger, more reliable traces than would traces in the IC, allowing more reliable routing to more conveniently placed, more durable, and larger mounting pads 718 than interconnection pads on the top face 207 of the "bare" IC 702. Since the secondary components mounted on redistributed surface 720 would normally use significant substrate surface area, the size and complexity of substrate 202 is minimized, which in turn minimizes the size of the device containing substrate 202 (or frees up space for other components).

Also, the number of connections between the IC and substrate is reduced or eliminated. Connections between off-chip components and the substrate are also reduced since off-chip components mounted to the redistributed surface 720 are thereby connected electrically to the IC, rather than being electrically connected by wire bonding through the substrate, as are components surface mounted to some "bare" ICs. Surface mounting components to the redistributed surface 720, rather than directly to the "bare" IC is also more reliable. For instance, mechanical stress on solder joints between a "bare" IC and a traditionally surface mounted component, induced by a thermal mismatch between the IC and the component, is alleviated.

Additionally, the ICs may be batch processed, as may placing components on the ICs, leading to increased efficiency, yield, and/or cost savings. In addition, this arrangement facilitates use of traditional, low-cost, reliable chip-and-wire technology for IC-to-substrate and secondary component-to-substrate connections.

Furthermore, space above a bare IC 702 that would ordinarily be unused is occupied by components that would otherwise increase the size of the device. The added layers on bare IC top face 207 also provide a damping media for protection against the stresses and damages caused by assembly handling and component placement. The IC and substrate being of similar length also increases the mechanical strength of the subassembly, which, e.g., increases yield through production processing.

The optional grounding plane 706 provides electronic shielding for sensitive components within IC 206, when needed. Since the redistribution brings interconnected circuits and components into close proximity, noise signals and voltage levels from the secondary components may potentially affect circuits within IC 206. Grounding plane 706, connected to a grounding pad (but not connected to any other interconnect pads), provides an isolated and quiet environment for electronics in IC 206.

Insulation layer 714 may potentially be created after secondary component(s) are mounted to mounting pad(s) 718. For instance, a non-conductive epoxy or the like may be used to encapsulate the bottom portion of a secondary component and surrounding areas where insulation is desired, such as on traces formed during creation of redistributed surface 720.

Using the top 204 of the substrate assembly 202n or each substrate panel 202, a non-conductive adhesive such as non-conductive epoxy is applied to attach each integrated circuit 206 as shown in FIG. 5. After the ICs 206 are assembled to substrate panels 202, each non-serialized IC 206 is uniquely identified by the serial number on substrates 202, and can be tested and calibrated with calibration information saved together with the serial number. For instance, test pads 719A (and/or pads 718, 719) may be used for testing at this point, as they may also have been used for testing of the ICs at wafer level. However, once the ICs are assembled to substrates, the calibration and test results may be saved with the respective serial numbers.

Figures 7A, 7B:
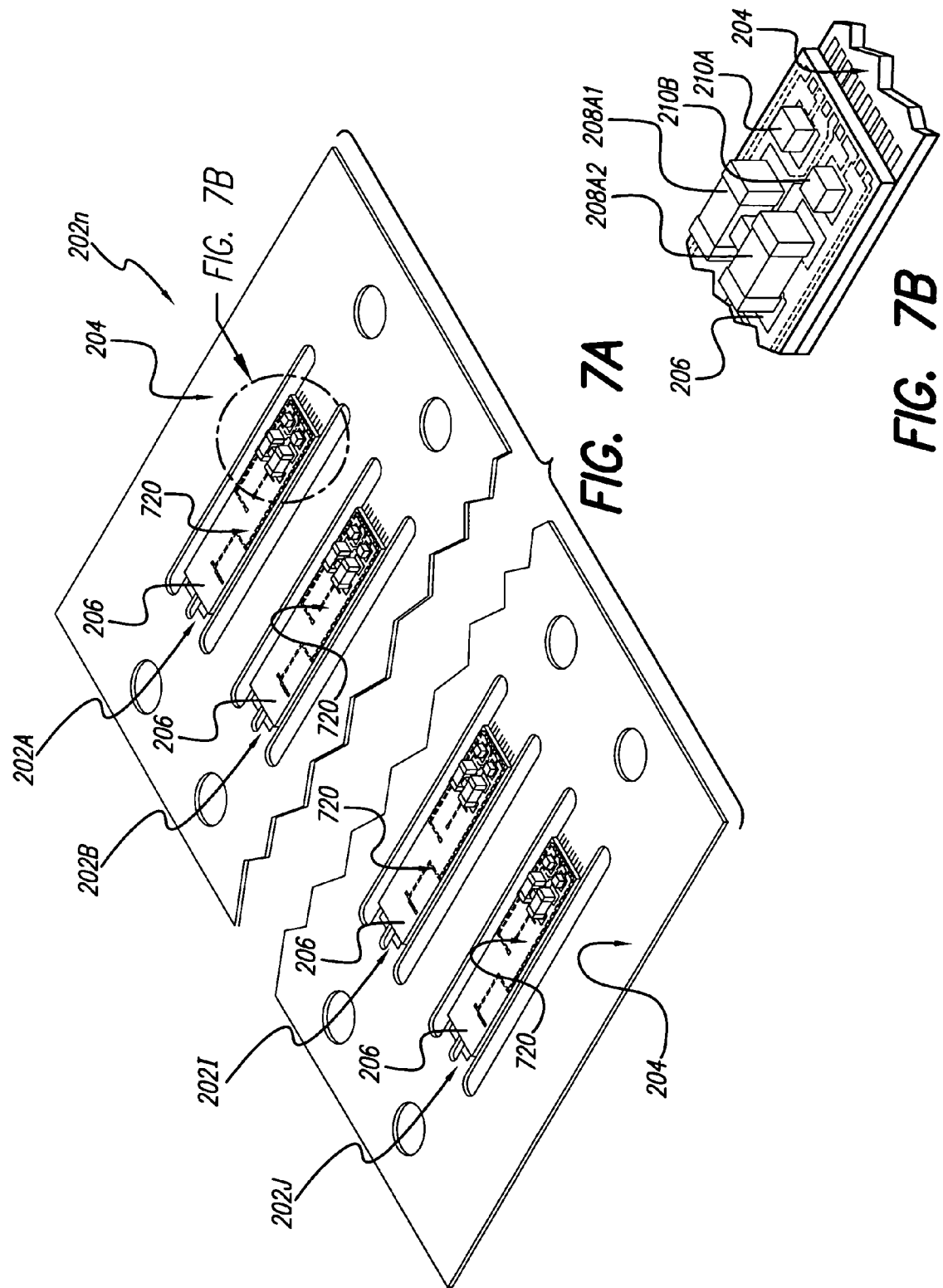
FIG. 7A is a perspective top view of the panel assembly shown in FIG. 5 with capacitors and diodes attached.
FIG. 7B is an enlarged detail view of some of the components shown in FIG. 7A.
Figure 8B:
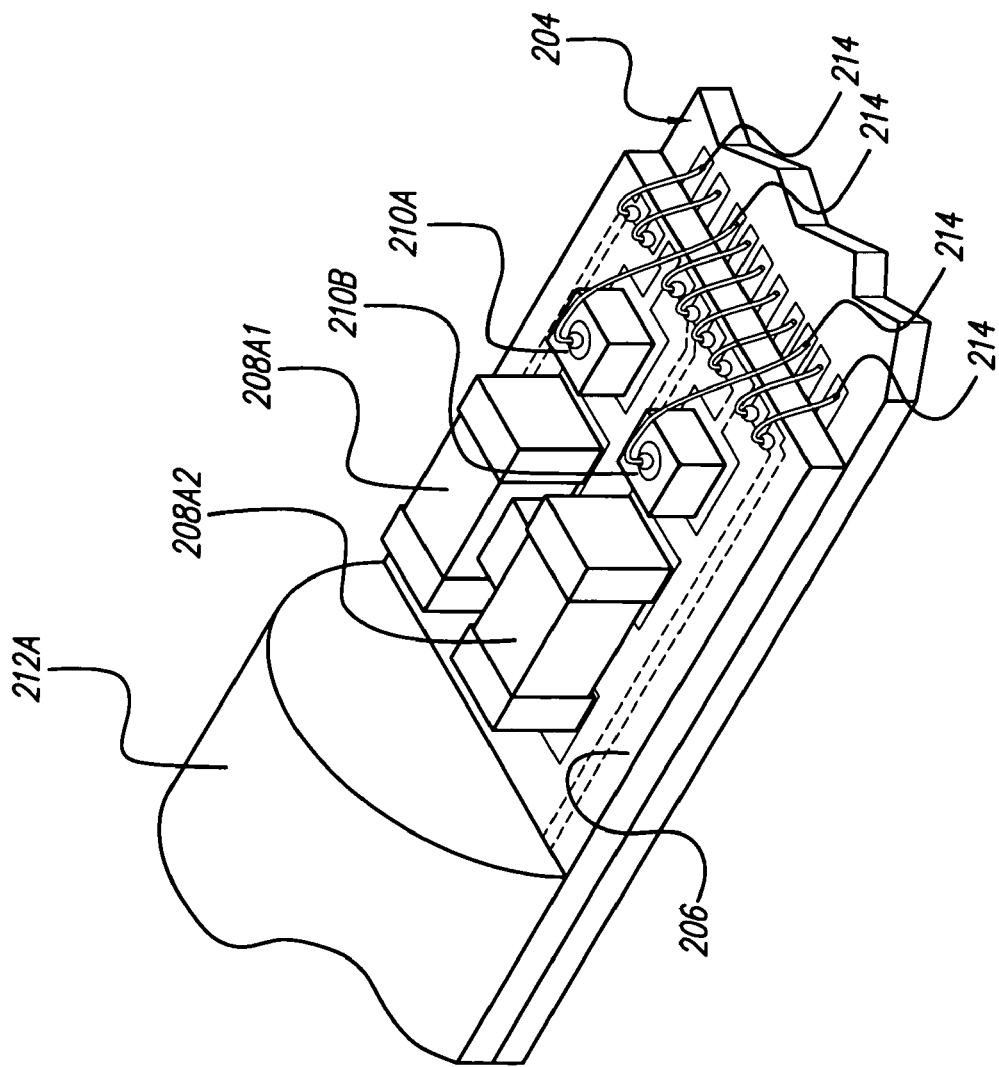
FIG. 8B is an enlarged detail view of some of the components shown in FIG. 8A including wire bond electrical connections.

Conductive epoxy or the like is used to attach off-chip components, e.g., capacitors 208A1, 208A2 and diodes 210A, 210B, to mounting pads 718 on the redistributed surface 720 of each IC 206, as shown in FIGS. 7A and 7B. As seen in FIG. 8A and in enlarged view in FIG. 8B, conductive wires 214, such as gold wires, electrically connect components (e.g., capacitors 208B1, 208B2) through the substrate to the IC. Wires 214 are attached to traces on the substrate top 204 and to pads 719 on the IC redistributed surface 720 via wire bonding. Similarly, wires 214A, such as gold wires, connecting traces on substrate top 204 to diodes 210A and 210B (which are already electrically connected to IC 206 through mounting pads 718 and redistribution surface 720) are attached via wire bonding.

Figure 9A:
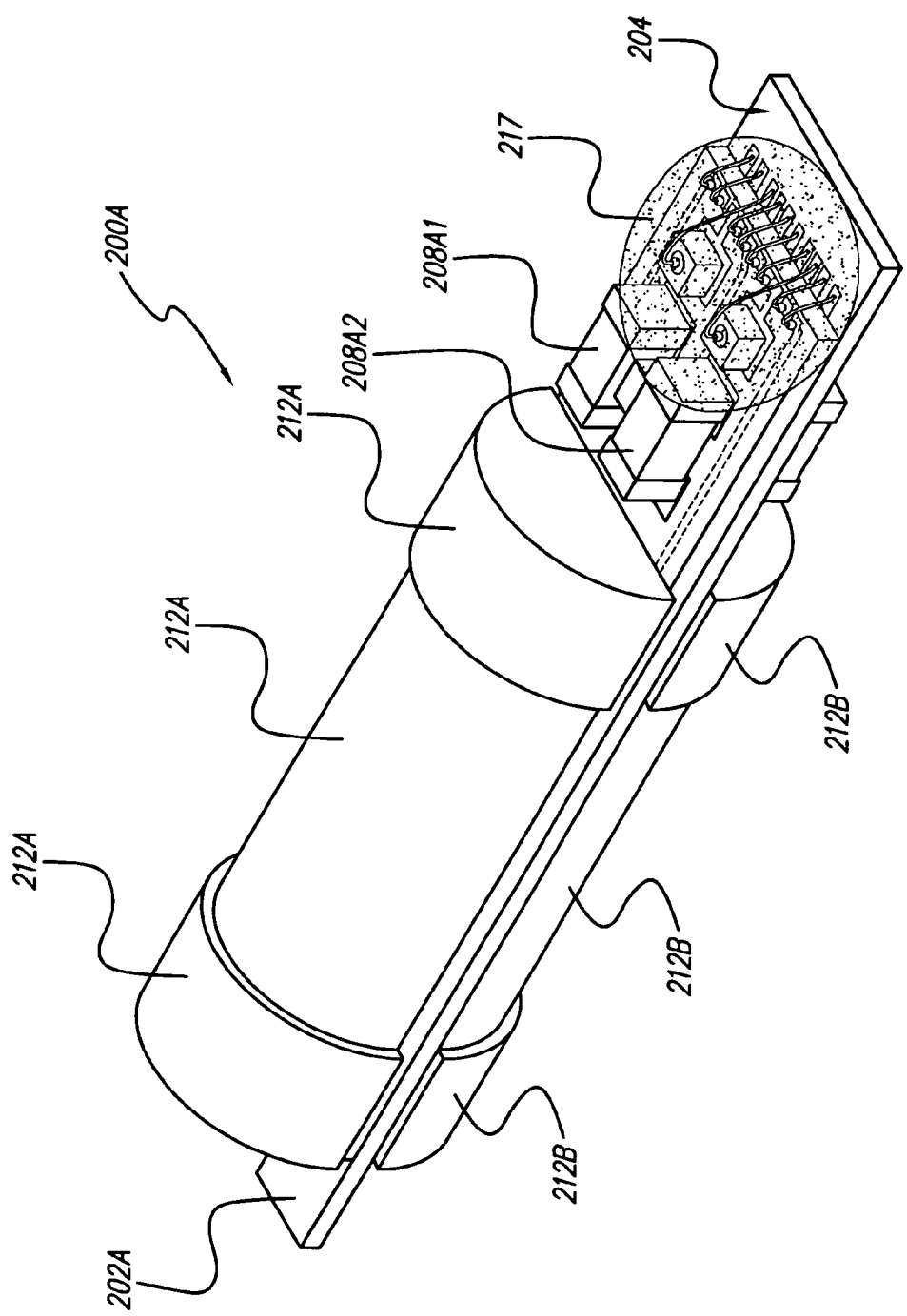
FIG. 9A is a isometric top view of a subassembly of the invention, including the wire bonds of FIG. 8B shown encapsulated with protective material.
Figure 9B:
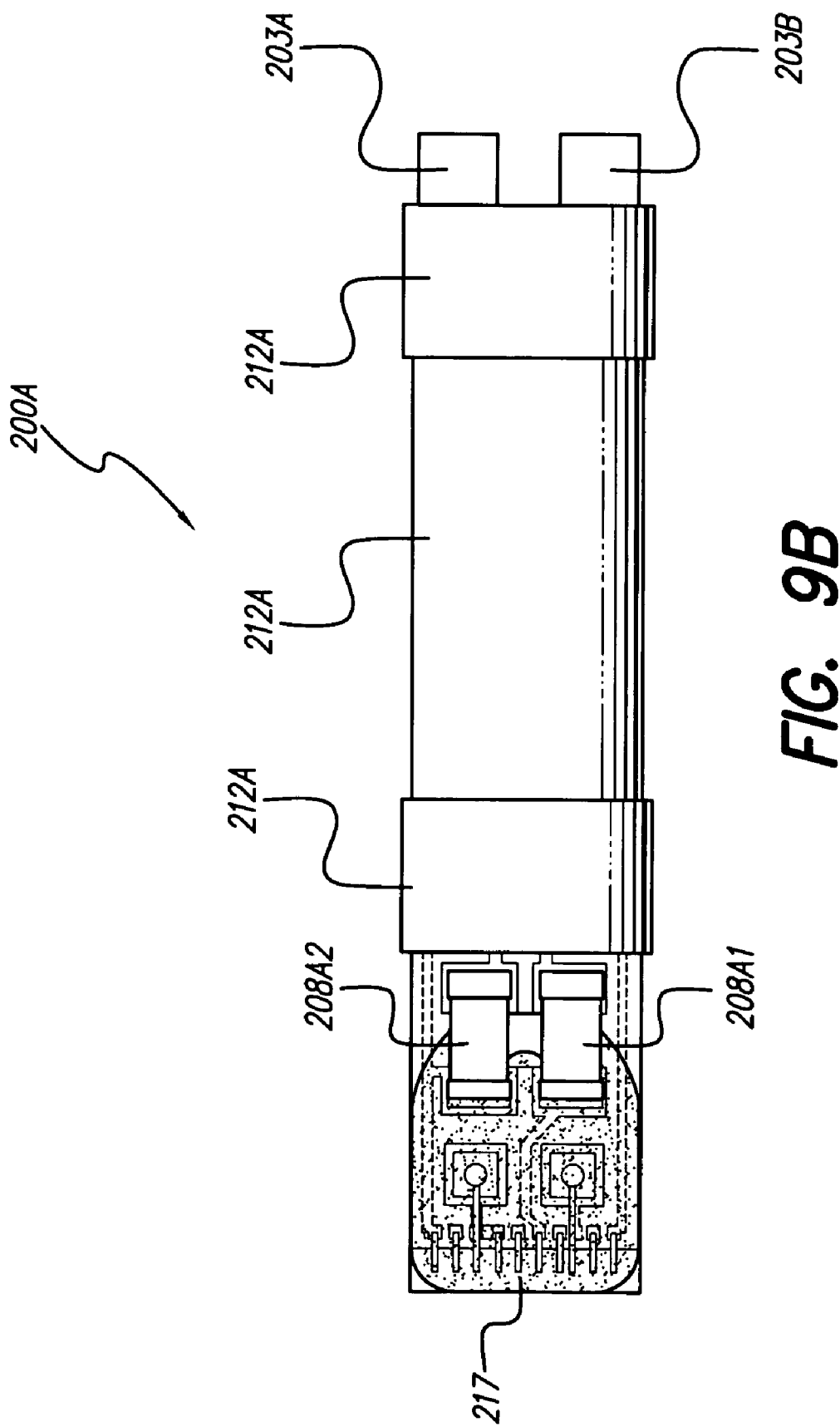
FIG. 9B is a plan view of the subassembly shown in FIG. 9A.

Quality inspection and testing (e.g., using test pads 719A) are typically performed at this point, as well as at other points in the manufacturing process. To protect wires 214, 214A from damage that may occur during the assembly and handling, the wires may be encapsulated, e.g., with an epoxy (such as Hysol®, available from Loctite of Rocky Hill, Conn.) or other non-conductive material 217, as shown in FIGS. 9A and 9B.

As seen, e.g., in FIGS. 1B, 9A, 1A, and 11B, ferrite half cylinders 212A and 212B "sandwich" a portion of panel 202 and a portion of associated integrated circuit 206. This design maximizes the length of ferrite (or other suitable core material) half cylinders 212A and 212B and diameter of the resulting ferrite core and coil 18, thus maximizing the magnetic inductance of the coil assembly. At the same time, since the ferrite halves "sandwich" IC 206 and substrate 202, the length of the housing is less than if these components were arranged in series. The sandwich design protects the IC and substrate while increasing the mechanical strength of the assembly. In addition, positioning IC 206 and substrate 202 between the ferrite halves allows the size of the IC (and substrate) to be maximized without lengthening the electronic subassembly 14 (and thus the device). Furthermore, the length of IC 206 (and substrate 202) is not limited to the length of the ferrite core; IC 206 can extend nearly the full length of electronic subassembly 14, allowing mounting of secondary components above IC 206 via redistributed surface 720.

By extending IC 206 through and beyond the ferrite core, it is possible to use a "one-chip" approach, thus avoiding the difficulties of processing two ICs. It is possible to use a two-IC approach, for instance, using flip-chip technology. However, using two chips potentially increases the number of interconnects, the size of the subassembly, and the difficulties of processing the subassembly. For instance, under-fill reinforcement may be difficult, while processing without under-fill reinforcement requires more placement accuracy, which may decrease efficiency, e.g., due to piece processing rather than batch processing.

In addition, as can be seen in the figures, core halves 212A and 212B form a core having a "dumbbell" shape. This shape further increases coil inductance by maximizing the ferrite material and diameter at the ends of the ferrite core. In addition, the dumbbell shape aids in the winding of wire 216 into coil 18 by acting as a mandrel, by constraining the wire to fit in the middle section of the dumbbell shape, and by centering the winding along the ferrite core. The dumbbell shape also helps to protect the wire of coil 18 during subsequent assembly steps. In addition, having a dumbbell shaped core achieves these goals while also facilitating creation of a cylindrically shaped device, which is the most efficient shape for some uses. For instance, a cylindrically shaped microstimulator 10 is ideally suited for insertion into a body through a cannula.

Figure 10B:
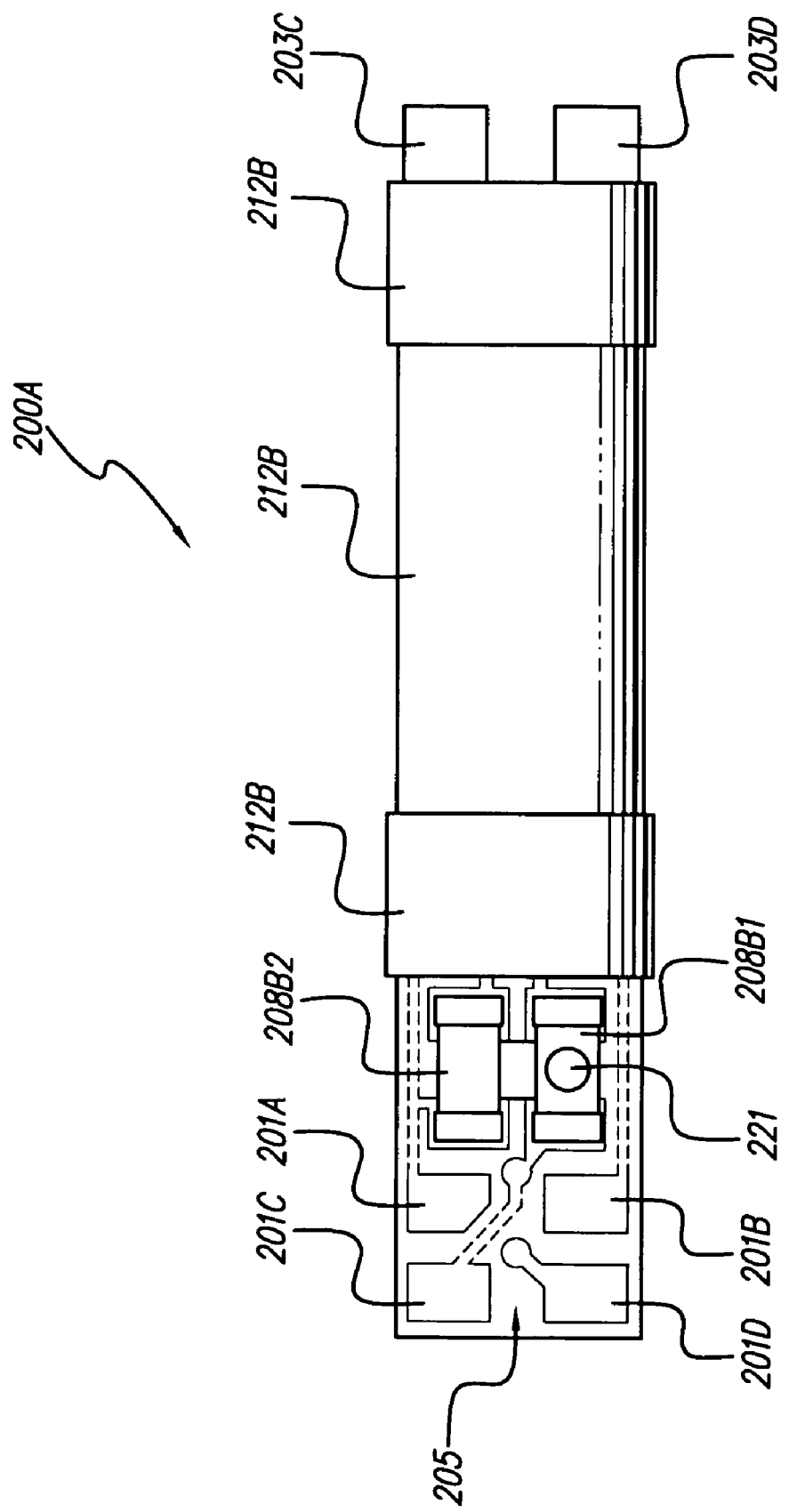
FIG. 10B is a plan view of the subassembly shown in FIG. 10A.

Non-conductive epoxy or other appropriate non-conductive adhesive is applied to bond top ferrite half 212A to a portion of IC redistributed surface 720, as shown in FIGS. 8A, 9A, and 9B. Similarly, non-conductive epoxy or the like is applied to bond bottom ferrite half 212B to a portion of substrate bottom 205, as shown in FIGS. 10A and 10B. Alternatively, the coil may hold the ferrite halves in place, so no or little adhesive material need be used.

Conductive adhesive such as conductive epoxy is applied to bond and electrically connect capacitors 208B1 and 208B2 to substrate mounting pads 730 (FIG. 4B) on the substrate bottom 205, as shown in FIGS. 10A and 10B. At this point in the assembly/manufacture process, partially assembled units 200A are typically separated from panel assembly 202n, e.g., by breaking away the pre-cut small portions made to contour the edge of each panel 202. Of course, panels 202 may be separated from panel assembly 202n by any useful means and at any useful point in assembly/manufacture.

FIGS. 9B and 10B show pads 203A, 203B, 203C, and 203D protruding from one end of the ferrite "sandwich" arrangement. Pads 203A and 203B are used to connect stimulating capacitor 15, as described below, and can also be used for testing. As described earlier, pads 203C and 203D carry the serial number and are also used for electrical test probing. (Connector pads 201A, 201B, 201C, and 201D (FIGS. 10A and 10B) may also be used for testing.) Also seen in FIGS. 10A and 10B is mark 221 (shown on capacitor 208B, but it may be placed wherever practical) which aids in orientation and handling during manufacturing.

Figure 11A:
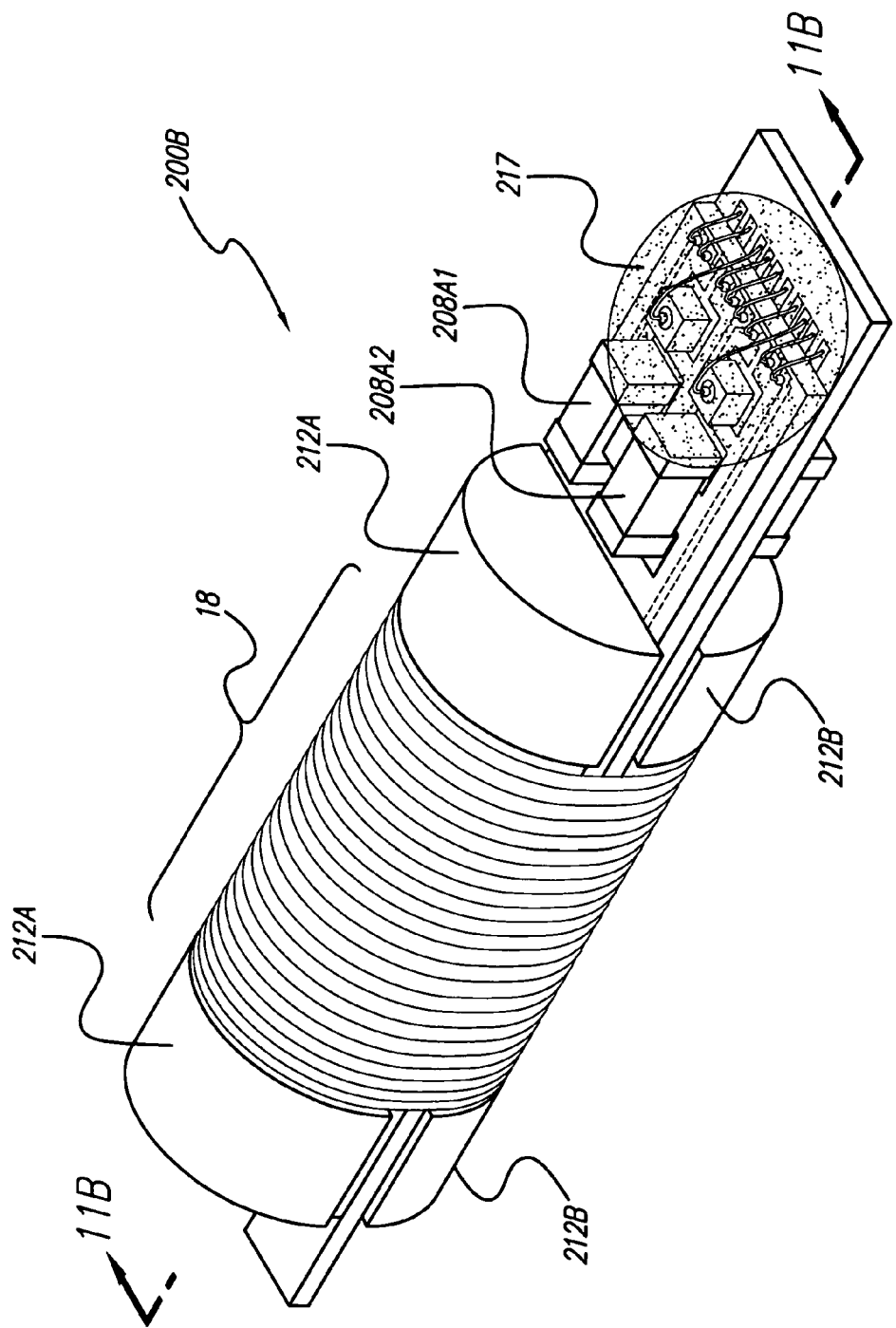
FIG. 11A is a perspective view of the subassembly shown in FIG. 9A with a coil wound on the middle section of the ferrite core.
Figure 11B:
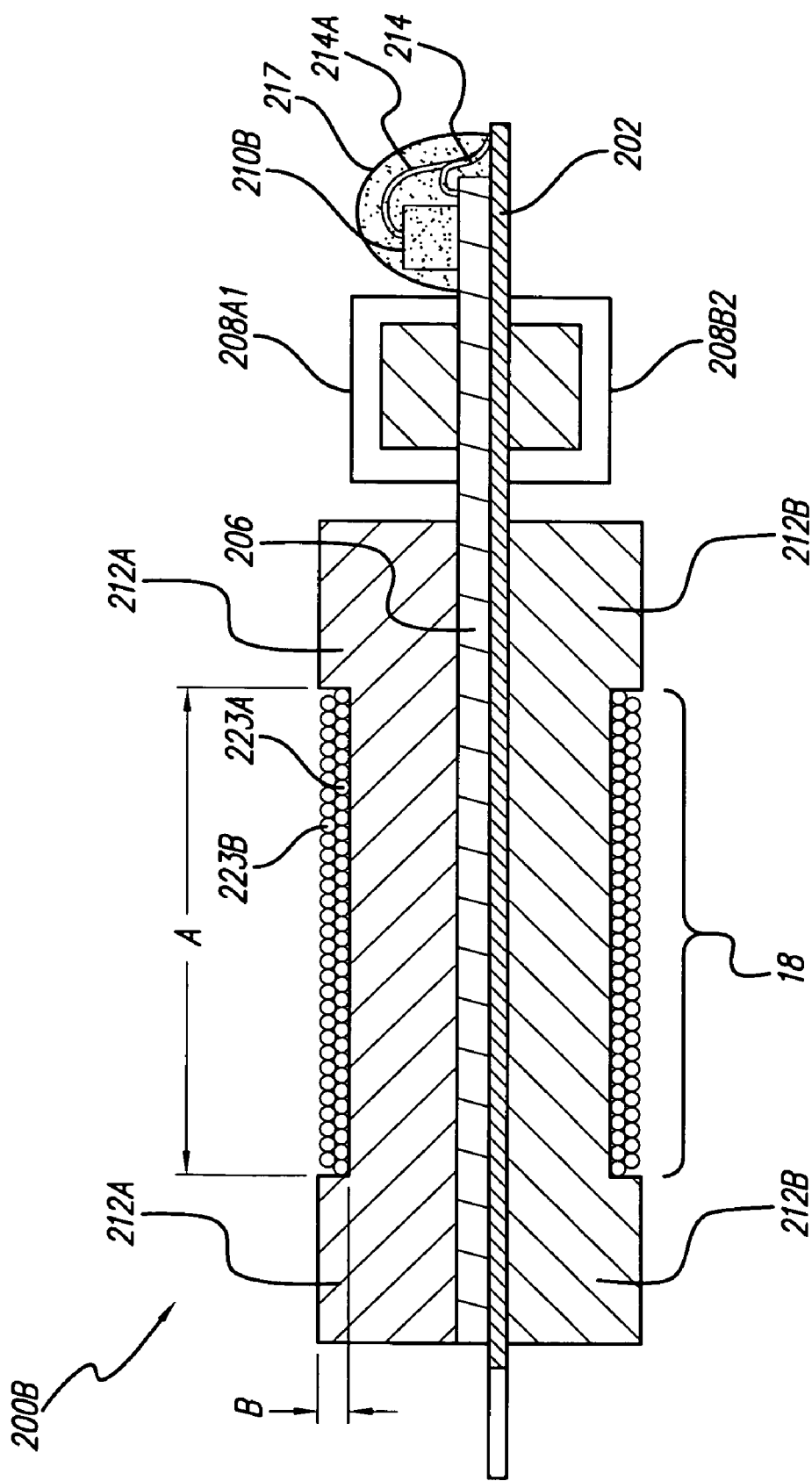
FIG. 11B is a cross-section view of the subassembly shown in FIG. 11A taken along line 11B-11B.

The unwound coil wire 216, made of 46 gauge insulated magnetic copper wire or other suitable conductive wire material, is wound on the middle section of the ferrite halves 212A and 212B (see FIGS. 11A and 11B). The coil wire 216 in a wound configuration is referred to as coil 18, as shown, e.g, in FIGS. 1B, 11A, and 11B. Coil 18 may have, for instance, 156 turns in two layers, identified in FIG. 11B as coil layer 223A and coil layer 223B. One coil layer or more than two coil layers may instead be used, as may a different number of turns in the winding. The number of turns and layers, and other design elements of the coil assembly, depend on the requirements of the coil assembly, such as frequency, current, and voltage. As shown in FIG. 11B and discussed earlier, an exemplary "dumbbell" configuration is formed with the arrangement of the two core halves 212A and 212B in which the gap formed by the distances A and B is used to wind coil 216. This configuration maximizes the size of the core and the coil (and IC 206 and substrate 202, as described earlier) in the constrained space of case 12, and aids in manufacturing.

Figure 11C:
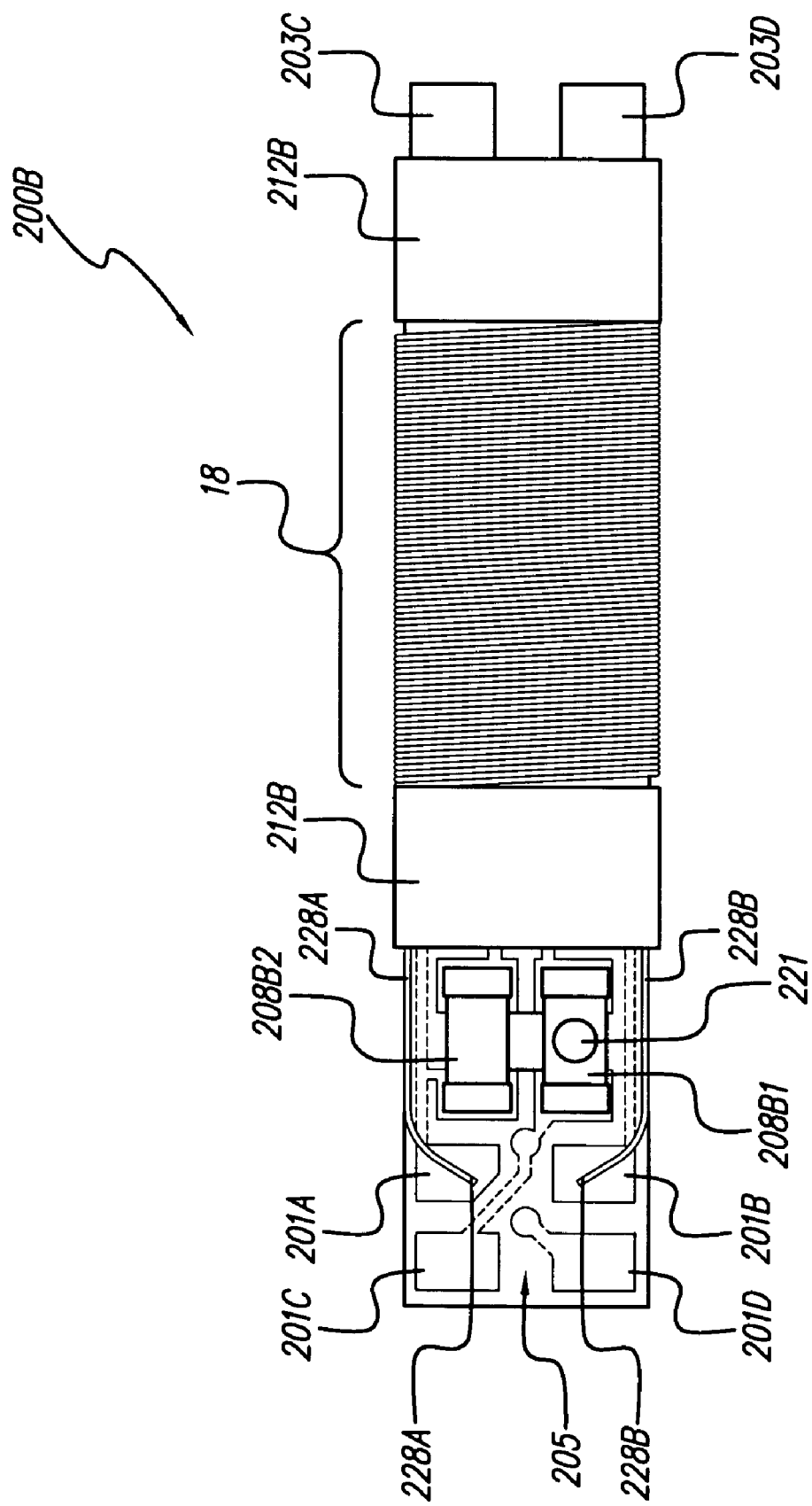
FIG. 11C is a bottom plan view of the subassembly shown in FIG. 11A with the coil ends depicted.
Figure 12:
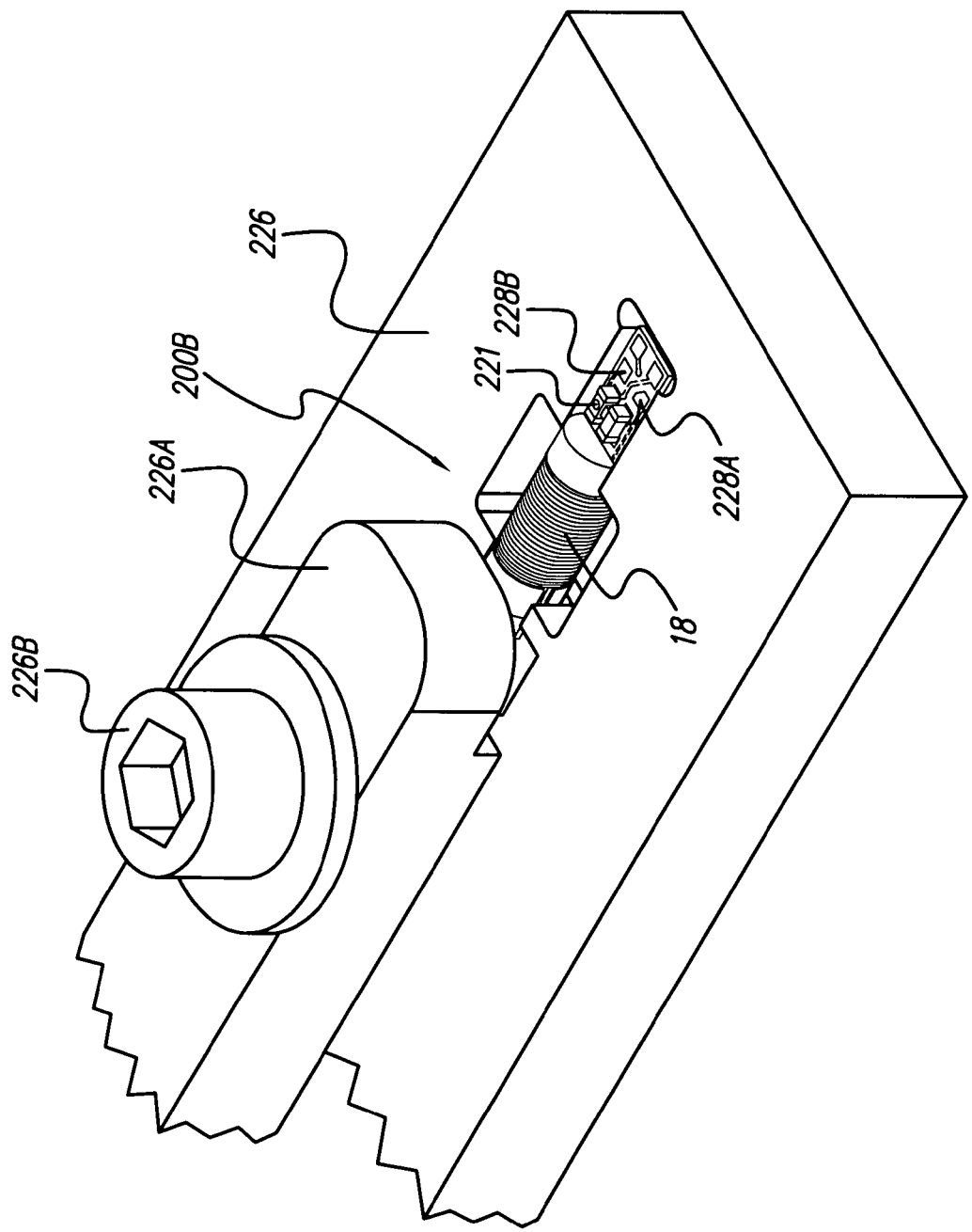
FIG. 12 is an enlarged detail perspective view of the subassembly shown in FIG. 11C placed in a soldering fixture.

A soldering fixture 226, shown in FIG. 12, may be used to assist in terminating the coil 18 ends 228A and 228B to pads 201A and 201B of panel 202 (FIG. 11C). Soldering coil ends 228A and 228B becomes more practical when the subassembly 200B is isolated and secured using soldering fixture 226 or other suitable fixture. Subassembly 200B is placed in fixture 226 with the bottom of panel 202 facing up, as identified by mark 221 or other orientation marker, and is held firmly in place, for instance, by handle 226A which is tightened by bolt 226B. FIG. 12 shows subassembly 200B securely loaded in soldering fixture 226. The two coil ends 228A and 228B are soldered or similarly connected to pads 201A and 201B, respectively. Tinning of pads 201C and 201D may also be performed at this time, and subassembly 200B may be baked prior to battery 16 attachment.

Figure 13A:
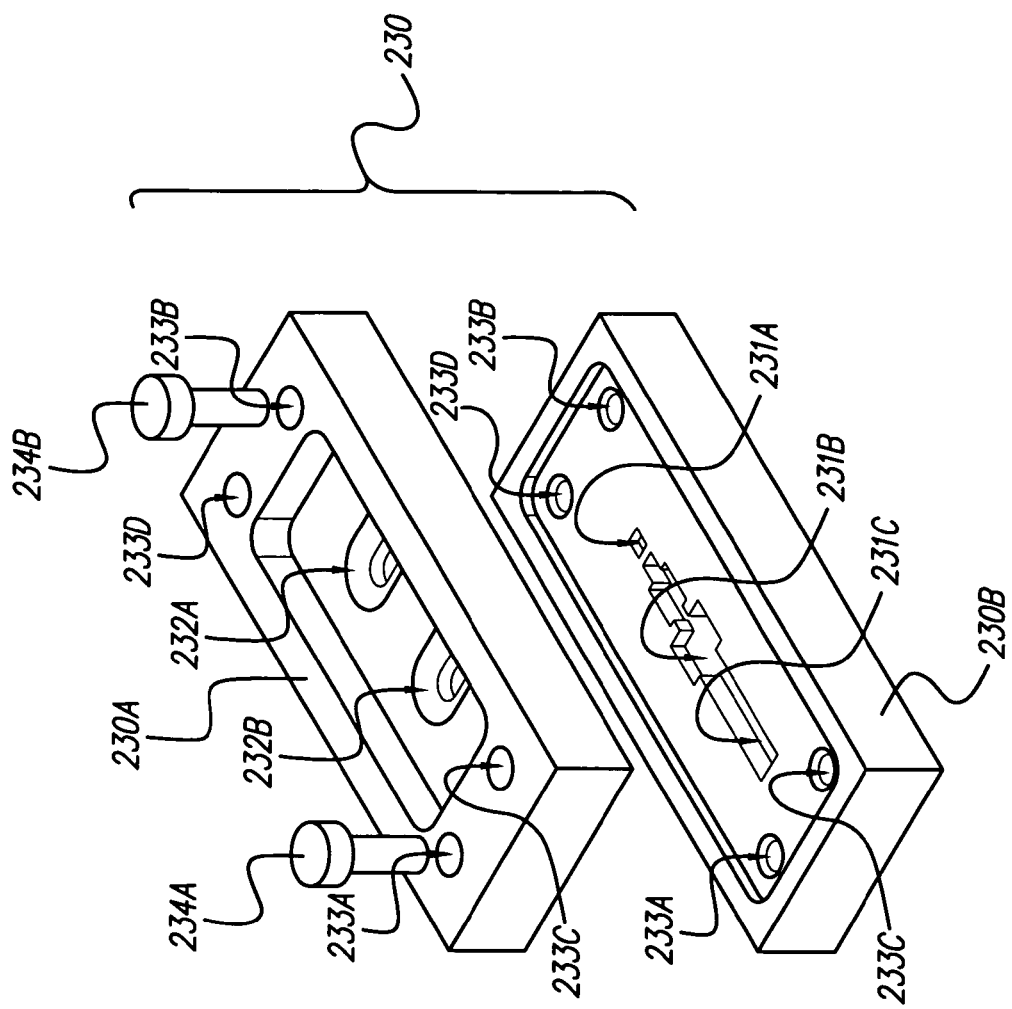
FIG. 13A is an exploded view of a carrier used during assembly.

A carrier 230, such as shown in FIG. 13A, can be used to facilitate further assembly processes by, for instance, aiding in concentric/coaxial alignment of components, serving as a dimensional control gauge, easing handling by effectively increasing the size of the device being handled, providing protection for sensitive components, allowing stacking of devices (e.g., within carriers during processing, baking, temperature cycling or other testing), and/or providing access for testing during various stages of assembly. Carrier 230 may be made of conductive or dissipative polyetherimide (such as Ultem®, available from GE Plastics of Pittsfield, Mass.), or other material to limit Electrical Static Discharge (ESD).

Figure 13B:
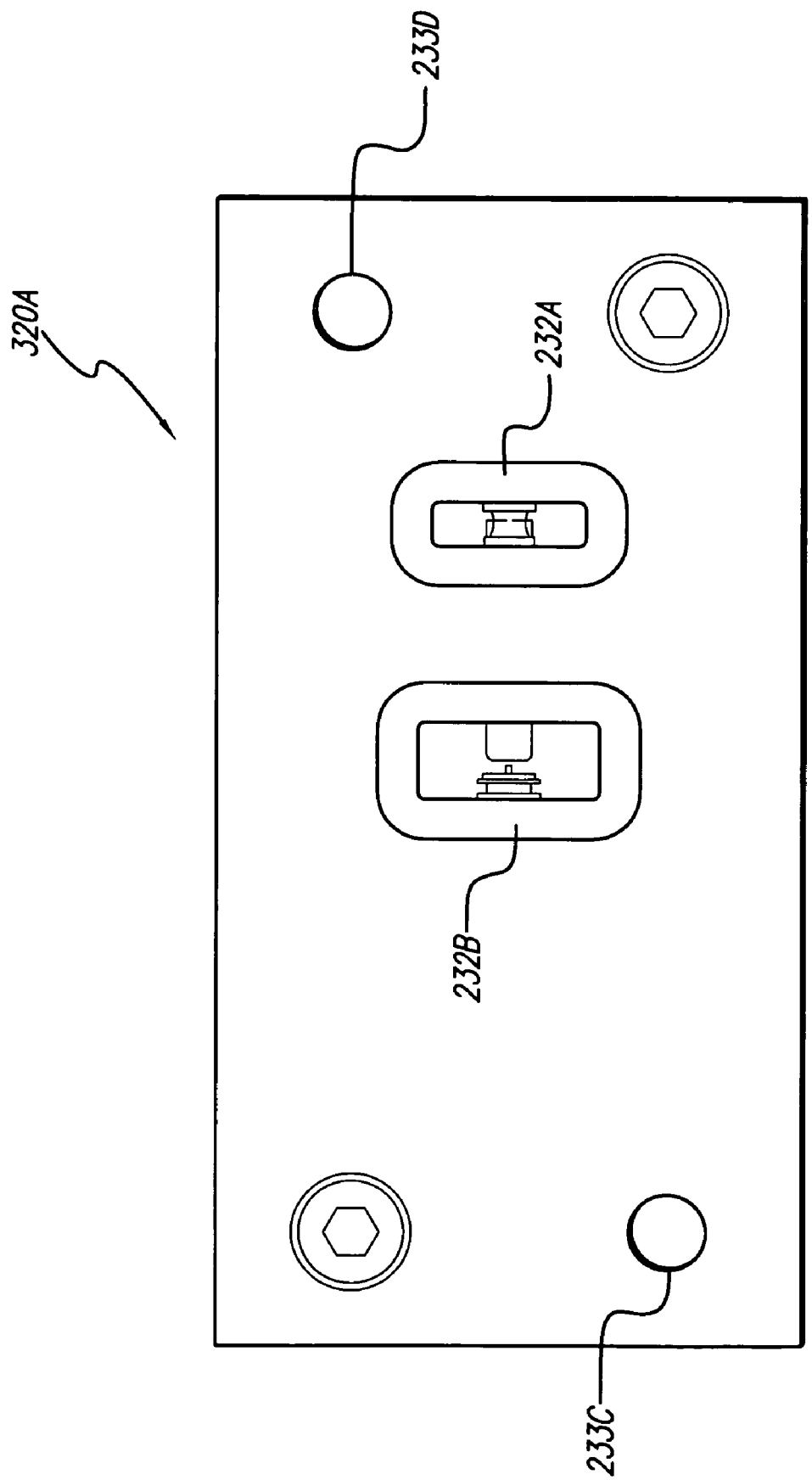
FIG. 13B is a top view of the top carrier plate of FIG. 13A.
Figure 13C:
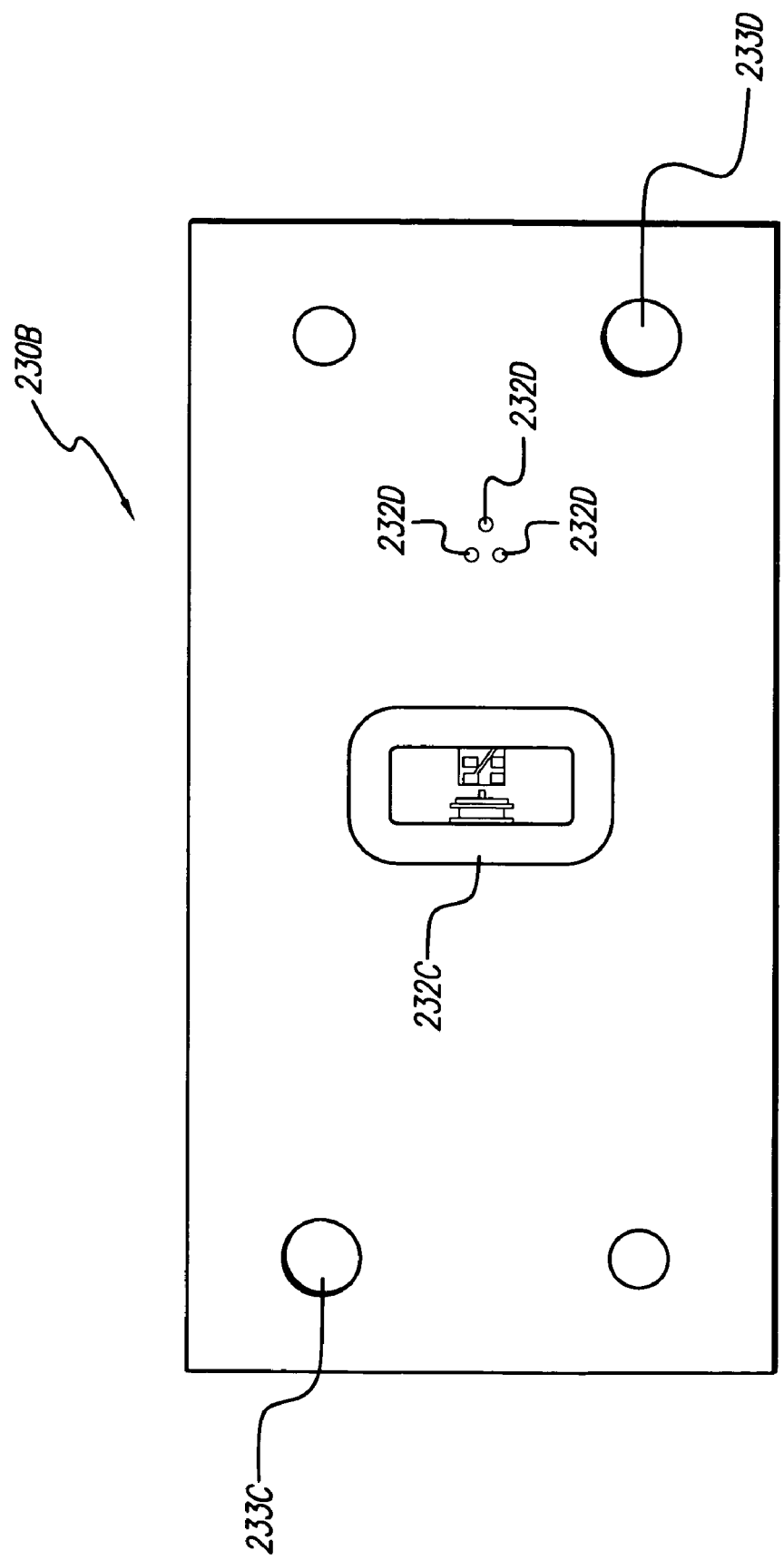
FIG. 13C is a bottom view of the bottom carrier plate of FIG. 13A.

Carrier 230 may comprise two plates: top plate 230A (FIGS. 13A and 13B) and bottom plate 230B (FIGS. 13A and 13C). Cavities 231A, 231B, and 231C (FIG. 13A) securely hold the partially assembled device when plates 230A and 230B are bolted (or otherwise coupled) together. Top plate 230A contains openings 232A and 232B and bottom plate 230B contains openings 232C and 232D to allow access to the device components for assembly, testing, and inspection. Plates 230A and 230B are securely fastened, e.g., with bolts 234A and 234B that align with holes 233A and 233B (FIG. 13A). If desired, carrier 230 (or bottom plate 230B) may be aligned and secured to a work plate 239 via holes 233C and 233D in carrier 230 and pins 237A and 237B on work plate 239 (see FIG. 14), or other suitable method. Having the carrier 230 aligned and secured to a work plate 239 may further facilitate portions of the assembly process.

Figure 14:
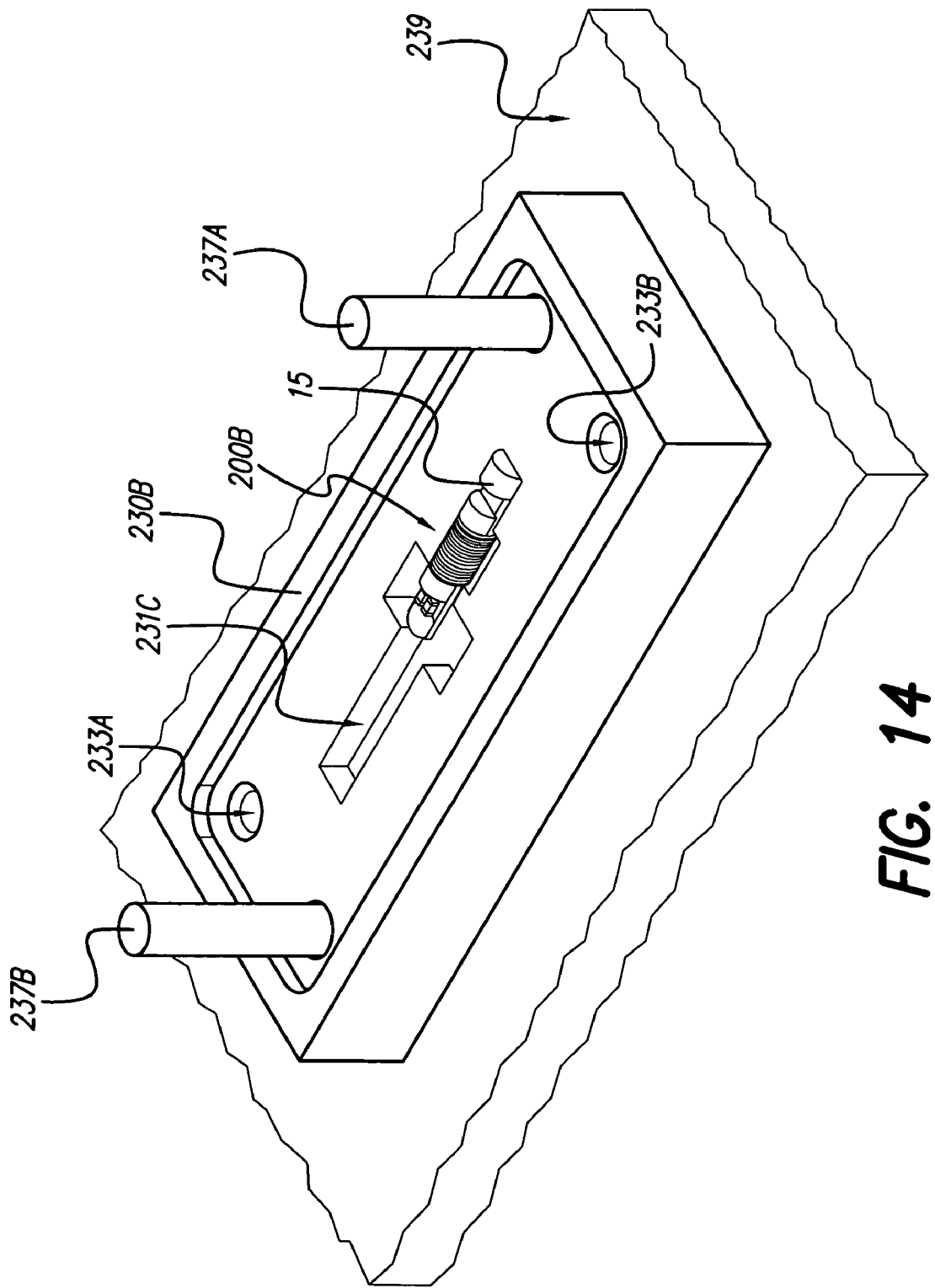
FIG. 14 is a perspective view of a work-plate supporting the bottom carrier plate of FIG. 13A, with the subassembly of FIG. 11A and a stimulating capacitor placed in the bottom carrier plate.

Subassembly 200B and stimulating capacitor 15 are placed in carrier bottom plate 230B as shown in FIG. 14, then top plate 230A is secured to bottom plate 230B, e.g., with bolts 234A and 234B. Stimulating capacitor 15 may be a tantalum capacitor, for instance, in which case it would preferably include a gold-plated nickel ribbon attached via resistance welding or the like to a tantalum pin protruding from one end of capacitor 15, as shown in FIG. 2A. If, as another example, a ceramic capacitor 15 is used, a ribbon would not be needed. Instead, a wire of stainless steel, nickel, copper, solder coated copper, or the like, protruding from one end of capacitor 15 may simply be bent to one side for attachment to pad(s) 203A/203B.

The type of stimulating capacitor 15 used may depend on the intended use of microstimulator 10. For instance, a tantalum capacitor may have a capacitance of approximately 7 microfarads, while a ceramic capacitor may have a capacitance of approximately 3 microfarads. The capacitor best suited to the requirements of the device in a given setting may thus be chosen. In any case, stimulating capacitor 15 is preferably a right circular cylinder that fits snugly within case 12.

Through opening 232A on top plate 230A, testing at pads 203A/203B (which are electrically connected) may be accomplished, then solder, conductive epoxy, or other suitable conductive adhesive 229 is applied (or other suitable method is used) to bond the ribbon or wire (or the like) of stimulating capacitor 15 to pad 203A and/or 203B. A material such as UV or thermal curable non-conductive epoxy 229A or the like may also be applied to reinforce the connection (see FIG. 16). Optionally, one or a portion of one of pads 203A/203B is left exposed for further testing. At this point, as at various points throughout the manufacturing process, the assembly is tested and processed through burn-in, baking, and temperature cycling while in carrier 230. For instance, opening 232C may be used to test at pads 201A, 201B, 201C, and/or 201D. Openings 232D may be used to test at pads 203C and 203D, and stimulating capacitor 15.

Figure 15:
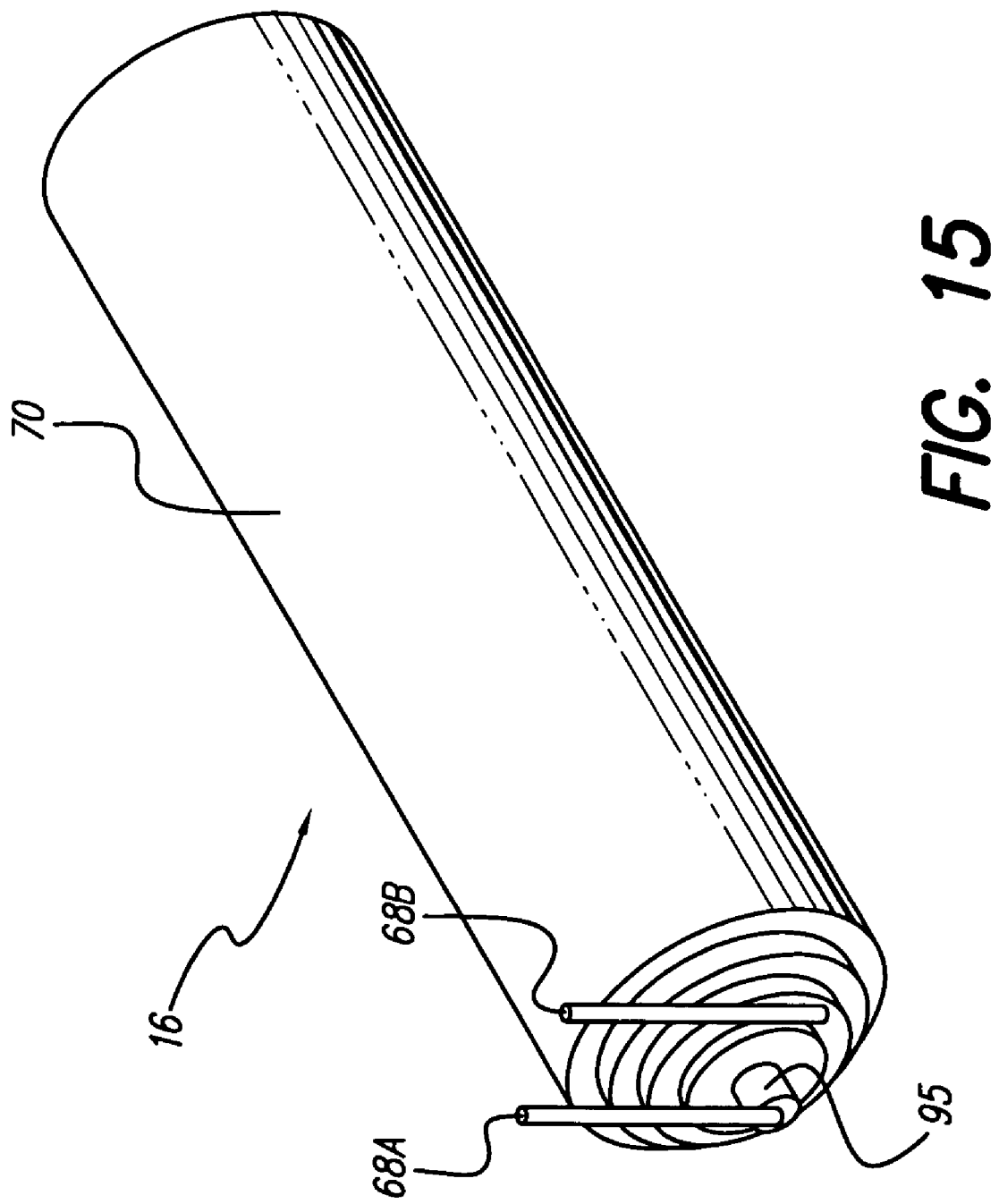
FIG. 15 is a perspective view of a battery with connecting wires.

If battery 16 was not previously placed in the carrier, top carrier plate 230A is removed, battery 16 is placed in cavity 231C of bottom plate 230B, and top plate 230A is fastened back in place. Battery 16, shown in FIG. 15, has a cathode (negative polarity) shell 70 and an anode (positive polarity) center pin 95 that protrudes, e.g., 0.25 mm from one end. Shell may be made of titanium, stainless steel, or other suitable cathodic material, while pin 95 may be made of platinum, molybdenum or other suitable anodic material. Two wires 68A and 68B made of nickel or the like are used for connecting battery 16 to electronic subassembly 14. Wire 68A is insulated (to prevent shorting) and laser welded or otherwise electrically connected to pin 95, and wire or ribbon 68B (insulated or not) is laser welded or otherwise electrically connected to the case of the battery.

Figure 16:
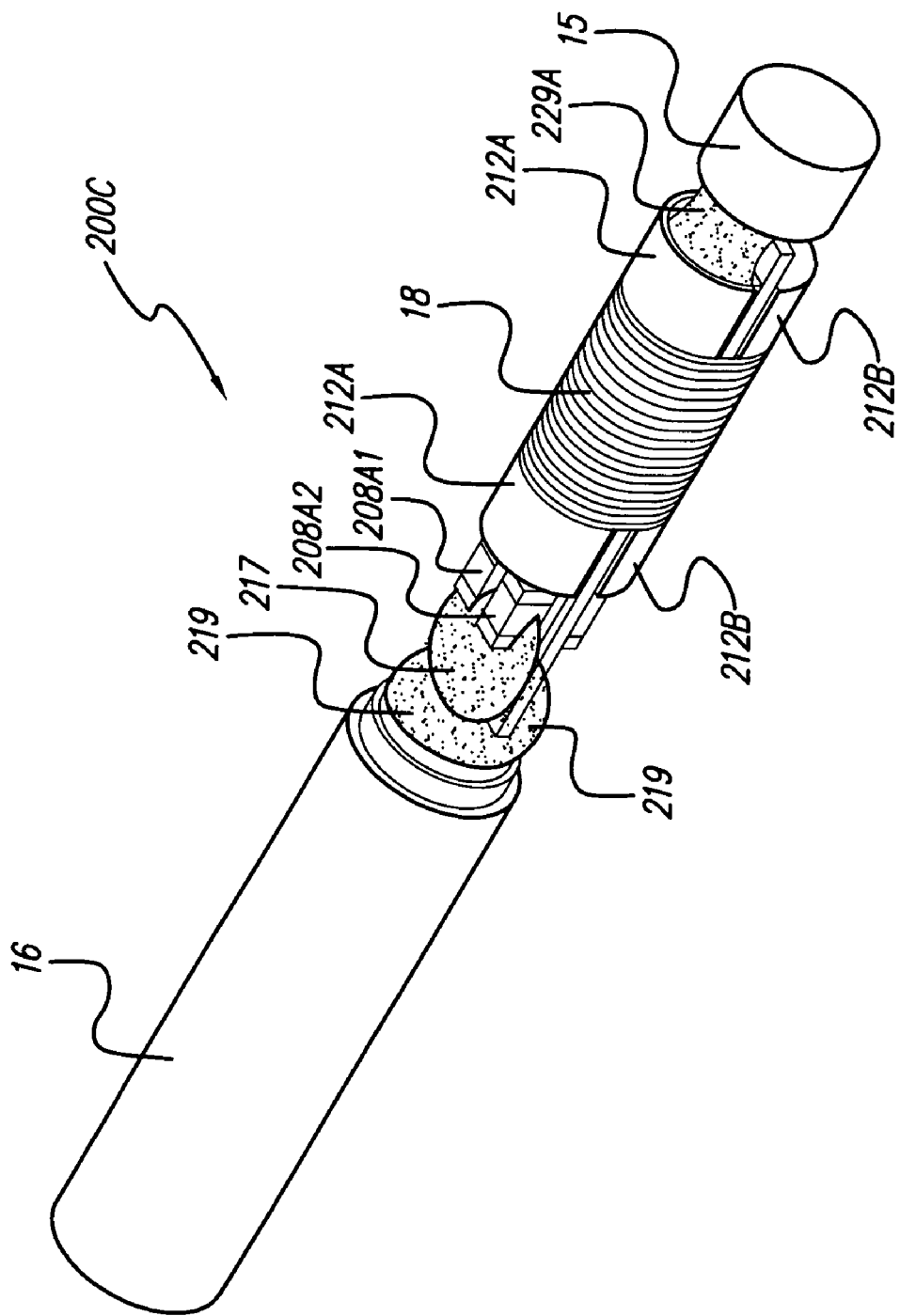
FIG. 16 is a perspective view of the subassembly of FIGS. 11A-11C with the battery of FIG. 15 and the stimulating capacitor of FIG. 14 attached.

Battery 16 is placed into cavity 231C so the long ends of wires 68A and 68B are pointing downwards (towards bottom plate 230B and bottom 205 of panel 202). Using opening 232B through top plate 230A, UV curable non-conductive epoxy 219 or the like is applied to reinforce the connection of the wires to the battery, while leaving the long ends of the wires 68A and 68B free. Carrier 230 is turned over so the free ends of wires 68A and 68B are accessible via opening 232C in bottom plate 230B. The free ends of wires 68A and 68B are trimmed, if necessary, and bent towards substrate 202. The free end of wire 68A is soldered to substrate pad 201D and the free end of wire 68B is soldered to substrate pad 201C. To complete subassembly 200C, as shown in FIG. 16, additional non-conductive epoxy 219 or the like may be applied to further secure the connection of wire 68A soldered to pad 201D and wire 68B soldered to pad 201C.

Once assembly 200C is complete, components 200 are contained within, e.g., housing 12 consisting of two cylindrical shells 213 and 215, as best seen in the cross sectional view of FIG. 1B. A variety of materials and shapes may be used for the housing. Via electrical attachment to stimulating capacitor 15, electrode 22 becomes the active or stimulating electrode. Shell 213 is electrically attached to the cathodic surface of battery 16, and a portion thereof may be formed, coated, plated, or otherwise processed with suitable material(s) to become the indifferent electrode 24, as shown in FIG. 1B. The device may be further processed with one or more coatings, or other post-assembly processes.

While the inventions herein disclosed have been described by means of specific embodiments and applications thereof, numerous modifications and variations could be made thereto by those skilled in the art without departing from the scope of the invention set forth in the claims. For instance, a number of the assembly/manufacturing procedures described may be performed in a different sequence than detailed herein. Some sequences were presented in an order most conducive to describing the general principles of the inventions, and should not be construed as limiting. Variations are within the scope of the inventions, as defined by the various claims.

What is claimed is:
1. An electronic module, comprising:
an integrated circuit having a top face with a plurality of first interconnect pads;
at least one redistribution layer adjacent to the top face of the integrated circuit, wherein the redistribution layer is electrically connected to the first interconnect pads and includes at least one conductive trace, at least one mounting pad, and a plurality of second interconnect pads, which second interconnect pads are positioned along at least one edge of the redistribution layer by the conductive traces;
at least one secondary component mounted to the at least one mounting pad and electrically connected to the integrated circuit via the redistribution layer;
a substrate including electrical traces terminating along at least one edge of the substrate; and
wire bonds connecting at least one of the second interconnect pads along at least one edge of the redistribution layer and at least one of the electrical traces along at least one edge of the substrate.

2. The electronic module of claim 1 wherein the at least one secondary component is at least one of a diode, a capacitor, a power source, and a coil.

3. The electronic module of claim 2 further comprising additional components electrically connected to the integrated circuit to form a microstimulator electronics package.

4. The electronic module of claim 1 further comprising a coil comprising a winding around a core;
the core comprising two separate halves;
one core half secured to a portion of the redistribution layer of the integrated circuit; and
a second core half secured to a portion of the substrate, wherein the core, when the two halves are assembled, is a dumbbell shape.

5. The electronic module of claim 1 wherein the at least one mounting pad is positioned at one end of the redistribution layer.

6. The electronic module of claim 1 wherein the redistribution layer comprises at least one of copper, polyimide, gold, and titanium tungsten.

7. The electronic module of claim 1 further comprising a first layer of insulation on at least some portions of the top face of the integrated circuit.

8. The electronic module of claim 7 wherein the redistribution layer includes:
a first layer of bond material on at least some portions of the integrated circuit;
a layer of conductive redistribution material on at least portions of the first bond layer; and
a second layer of bond material on at least some portions of the redistribution material.

9. The electronic module of claim 8 wherein the first bond layer covers portions of the integrated circuit and portions of the first insulation layer, and wherein the conductive redistribution material covers the first bond layer, and wherein the second bond layer covers the redistribution material.

10. The electronic module of claim 7 further comprising:
a grounding layer comprising at least a layer of shielding material above at least some portions of the integrated circuit.

11. The electronic module of claim 10 wherein the grounding layer includes:
a first layer of grounding bond material on at least some portions of the integrated circuit;
a layer of shielding material on at least some portions of the first grounding bond layer; and
a second layer of grounding bond material on at least some portions of the shielding material.

12. The electronic module of claim 11 wherein the first layer of grounding bond material covers portions of the integrated circuit and portions of the first insulation layer, and wherein the layer of shielding material covers the first grounding bond layer, and wherein the second grounding bond layer covers the layer of shielding material.

13. An electronic module, comprising:
a substrate including first traces;
an integrated circuit having a bottom face affixed to the substrate and top face with a plurality of first interconnect pads;
a redistribution layer proximate to the top face of the integrated circuit, the redistribution layer comprising second traces connected to the plurality of first interconnect pads, each second trace terminating at either a mounting pad or a second interconnect pads on a top of the redistribution layer; and
at least one secondary component mounted to the at least one mounting pad and electrically connected to the integrated circuit via the redistribution layer,
wherein at least one of the second interconnect pads is coupled to the first traces on the substrate.

14. The electronic module of claim 13, wherein the at least one of the second interconnect pads is coupled to at least some of the first traces on the substrate using a wire bond.

15. The electronic module of claim 13, wherein the at least one secondary component is electrically coupled to at least some of the first traces on the substrate.

16. The electronic module of claim 13, further comprising a coil coupled to at least some of the first traces on the substrate, wherein the communication coil is wound around the substrate, the integrated circuit, and redistribution layer, and the at least one secondary component.

17. The electronic module of claim 16, wherein the coil is additionally wound around a ferrite core.

18. The electronic module of claim 16, wherein the coil is configured to wirelessly receive either data, power, or both from an external device.

19. The electronic module of claim 13, wherein the redistribution layer comprises a grounding layer.

20. The electronic module of claim 13, further comprising a battery coupled to at least some of the first traces on the substrate.

21. The electronic module of claim 13, wherein the redistribution layer is bonded to the top face of the integrated circuit.

22. An electronic module, comprising:
an integrated circuit having a top face with a plurality of first interconnect pads
at least one redistribution layer adjacent to the top face of the integrated circuit, wherein the redistribution layer is electrically connected to the first interconnect pads and includes at least one conductive trace, at least one mounting pad, and a plurality of second interconnect pads, which second interconnect pads are positioned along at least one edge of the redistribution layer by the conductive traces;
at least one secondary component mounted to the at least one mounting pad and electrically connected to the integrated circuit via the redistribution layer;
a substrate including electrical traces terminating along at least one edge of the substrate; wire bonds connecting at least one of the second interconnect pads along at least one edge of the redistribution layer and at least one of the electrical traces along at least one edge of the substrate;
a coil comprising a winding around a core;
the core comprising two separate halves;
one core half secured to a portion of the redistribution layer; and
a second core half secured to a portion of the substrate.

* * * * *

UNITED STATES PATENT AND TRADEMARK OFFICE
CERTIFICATE OF CORRECTION

PATENT NO. : 7,640,061 B2 Page 1 of 1
APPLICATION NO. : 11/545334
DATED : December 29, 2009
INVENTOR(S) : He et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 571 days.

Signed and Sealed this

Twelfth Day of October, 2010

David J. Kappos
*Director of the United States Patent and Trademark Office*